(12) United States Patent
Frankish et al.

(10) Patent No.: US 9,586,885 B2
(45) Date of Patent: Mar. 7, 2017

(54) COMPOUNDS FOR USE IN THE TREATMENT OF INFLAMMATORY BOWEL DISEASE

(75) Inventors: Neil Frankish, Dublin (IE); Helen Sheridan, Dublin (IE)

(73) Assignee: Venantius Limited, Dublin (IE)

( * ) Notice: Subject to any disclaimer, the term of this patent is extended or adjusted under 35 U.S.C. 154(b) by 8 days.

(21) Appl. No.: 14/124,937

(22) PCT Filed: Jul. 20, 2012

(86) PCT No.: PCT/IE2012/000037
§ 371 (c)(1),
(2), (4) Date: Dec. 9, 2013

(87) PCT Pub. No.: WO2013/014659
PCT Pub. Date: Jan. 31, 2013

(65) Prior Publication Data
US 2014/0128466 A1 May 8, 2014

Related U.S. Application Data

(60) Provisional application No. 61/510,628, filed on Jul. 22, 2011.

(51) Int. Cl.
| | | |
|---|---|---|
| *C07C 65/19* | (2006.01) | |
| *C07C 215/06* | (2006.01) | |
| *A61K 31/192* | (2006.01) | |
| *A61K 9/00* | (2006.01) | |
| *A61K 47/26* | (2006.01) | |
| *A61K 47/38* | (2006.01) | |

(52) U.S. Cl.
CPC ............ *C07C 65/19* (2013.01); *A61K 9/0095* (2013.01); *A61K 31/192* (2013.01); *A61K 47/26* (2013.01); *A61K 47/38* (2013.01); *C07C 215/06* (2013.01); *C07B 2200/07* (2013.01)

(58) Field of Classification Search
USPC .................................. 514/555, 569; 562/466
See application file for complete search history.

(56) References Cited

U.S. PATENT DOCUMENTS

| 6,300,376 B1 * | 10/2001 | Walsh et al. ................. 514/680 |
| 2002/0128256 A1 | 9/2002 | Brugnara et al. |
| 2010/0152220 A1 | 6/2010 | Raymond et al. |

FOREIGN PATENT DOCUMENTS

| DE | 19619036 A1 | 11/1997 |
| WO | WO 97/20802 A1 | 6/1997 |
| WO | WO 2013/014660 A1 | 1/2013 |
| WO | WO 2013/174916 A1 | 11/2013 |
| WO | WO 2013/174917 A1 | 11/2013 |

OTHER PUBLICATIONS

Lobaton, Review article: anti-adhesion therapies for inflammatory bowel disease, Aliment Pharmacol Therapy 2014, 39, pp. 579-594).*
Neil Frankish et al, "6-(Methylamino)hexane-1,2,3,4,5-pentanol 4-(((1S,2S)-1-Hydroxy-2,3-dihydro-1H,1′H-[2,2-biinden]-2-yl)methyl)benzoate (PH46A): A Novel Small Molecule With Efficacy in Murine Models of Colitis", Journal of Medicinal Chemistry, American Chemical Society, Jun. 4, 2012.
Bernstein et al., "Epidemiology of Crohn's Disease and Ulcerative Colitis in a Central Canadian Province: A Population-based Study," *Am. J. Epidemiology*, vol. 149, No. 10 (1999).
International Search Report for PCT/IE2012/000037, dated Nov. 19, 2012 (3 pages).
International Search Report for PCT/IE2012/000038, dated Oct. 9, 2012 (3 pages).
International Search Report for PCT/EP2013/060614, dated Jul. 29, 2013 (5 pages).
International Search Report for PCT/EP2013/060613, dated Aug. 27, 2013 (3 pages).
Jordan, V.C. "Tamoxifen: A Most Unlikely Pioneering Medicine," *Nature Rev.*, vol. 2, pp. 205-213 (2003).
Katzman, S.D. et al, "Opposing Functions of IL-2 and IL-7 in the Regulation of Immune Responses," *Cytokine*, vol. 56, No. 1, pp. 116-121 (2012).
Passante, E. et al., "In Vitro Inhibition of Rat Basophilic Leukaemia Mast Cell (RBL-2H3) Degranulation by Novel Indane Compounds," *Inflamm. Res., Suppl. 1*, vol. 57, pp. S15-S16 (2008).
Sadlack, B. et al., "Ulcerative Colitis-like Disease in Mice with a Disrupted Interleukin-2 Gene," *Cell Press*, vol. 75, pp. 253-261 (1993).
Sheridan, H. et al., "Diastereoisomers of 2-benzyl-2, 3-dihydro-2-(1H-inden-2-yl)-1H-inden-1-ol: Potential Anti-inflammatory Agents," *Bioorg. Med. Chem. Lett.*, vol. 19, No. 20, pp. 5927-5930 (2009).
Cipolla, G. et al., "Nonsteroidal Anti-Inflammatory Drugs and Inflammatory Bowel Disease: Current Perspectives," *Pharm. Res.*, vol. 46, No. 1, pp. 1-6 (2002).
Henderson, W.R. et al., "The Importance of Leukotrienes in Airway Inflammation in a Mouse Model of Asthma," *J. Exp. Med.*, vol. 184, pp. 1483-1494 (1996).
Ishii, K. et al., "A Useful Method for Differential Evaluation of Anti-Inflammatory Effects Due to Cyclooxygenase and 5-Lipoxygenase Inhibitions in Mice," *Jpn. J. Pharmacol.*, vol. 65, pp. 287-303 (1994).
Kimura, I. et al., "Study on the Experimental Ulcerative Colitis (UC) Model Induced by Dextran Sulfate Sodium (DSS) in Rats (2)," *Nihon Yakurigaku Zasshi*, vol. 105, No. 3, pp. 145-152 (1995), abstract (1 page).

(Continued)

*Primary Examiner* — Kathrien Cruz
(74) *Attorney, Agent, or Firm* — Bookoff McAndrews, PLLC

(57) ABSTRACT

Described are compounds of the structural formula (I): Also provided are pharmacologically acceptable isomers and salts of the compound of (I). The compounds are useful in the treatment of inflammatory bowel disease.

10 Claims, 15 Drawing Sheets

(56) References Cited

OTHER PUBLICATIONS

Klein, A. et al., "Non Steroidal Anti-Inflammatory Drugs and Inflammatory Bowel Disease," *Pharmaceuticals*, vol. 3, pp. 1084-1092 (2010).
Musumba, C. et al., "Review Article: Cellular and Molecular Mechanisms of NSAID—induced Peptic Ucers," *Aliment. Pharmacol. Ther.*, vol. 30, pp. 517-531 (2009).
Okayama, M. et al., "Aggravation by Selective COX-1 and COX-2 Inhibitors of Dextran Sulfate Sodium (DSS)—Induced Colon Lesions in Rats," *Dig. Dis. Sci.*, vol. 52, pp. 2095-2103 (2007).
Sheridan, H. et al., "Synthesis and Antispasmodic Activity of Analogues of Natural Pterosins," *Eur. J. Med. Chem.*, vol. 34, pp. 953-966 (1999).
Tanaka, K. et al., "Inhibition of Both COX-1 and COX-2 and Resulting Decrease in the Level of Prostaglandins E2 is Responsible for Non-steroidal Anti-Inflammatory Drug (NSAID)—Dependent Exacerbation of Colitis," *Eur. J. Pharmacol.*, vol. 603, p. 120-132 (2009).
Tsubouchi, R. et al., "Healing Impairment Effect of Cyclooxygenase Inhibitors on Dextran Sulfate Sodium-Induced Colitis in Rats," *Digestion*, vol. 74, pp. 91-100 (2006).

\* cited by examiner

COMPOUNDS FOR USE IN THE TREATMENT OF INFLAMMATORY BOWEL DISEASE

This is a national stage of PCT/IE12/000037 filed Jul. 20, 2012 and published in English, which has a U.S. priority of No. 61/510,628, filed Jul. 22, 2011, hereby incorporated by reference.

This invention relates to new compounds for use in the treatment of inflammatory bowel disease.

INTRODUCTION

Inflammatory bowel disease (IBD) consists of two idiopathic inflammatory diseases, ulcerative colitis (UC) and Crohn's disease (CD). The greatest distinction between UC and CD is the range of inflamed bowel tissue. Inflammation in CD is discontinuously segmented, known as regional enteritis, while UC is superficial inflammation extending proximally and continuously from the rectum. At present, the exact cause of IBD is unknown. The disease seems to be related to an exaggerated mucosal immune response to infection of the intestinal epithelium because of an imbalance of pro-inflammatory and immune-regulatory molecules. The inheritance patterns of IBD suggest a complex genetic component of pathogenesis that may consist of several combined genetic mutations. Currently no specific diagnostic test exists for IBD, but as an understanding of pathogenesis is improved so will our testing methods. Treatment of IBD consists of inducing and maintaining remission. IBD patients may be maintained on remission by use of a 5-aminosalycilate. However, while the use of aminosalyciates in UC provides considerable benefit, both in inducing remission in mild to moderate disease and in preventing relapse, the usefulness of these drugs to maintain remission in CD is questionable and is no longer recommended. The mainstay of treatment of active disease is a corticosteroid, commonly used for limited periods to return both UC and CD patients to remission, though budesonide, designed for topical administration with limited systemic absorption, has no benefit in maintaining remission. Alternatives, such as the immunosuppressive drugs azathioprine and mercaptopurine, together with methotrexate and cyclosporine have limited efficacy and the capability of inducing grave adverse effects. Anti-TNFα antibodies, such as infliximab and adalimubab, may be used in those patients unresponsive to standard immunosuppressive therapy. However, many patients fail to respond to anti-TNFα therapy, either due to their particular phenotype or by the production of autoantibodies.

STATEMENTS OF INVENTION

In accordance with the present invention there are provided compounds for use in the treatment of inflammatory bowel disease including Crohn's disease and ulcerative colitis.

In particular, the present invention provides compounds of the structural formula I:

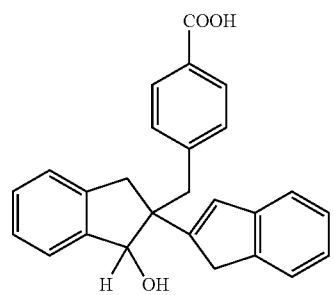

(I)

Also provided are pharmacologically acceptable isomers and salts of the compound of formula (I)—compound 1.

In particular, the present invention provides compounds of relative stereochemistry as demonstrated in structural formula II:

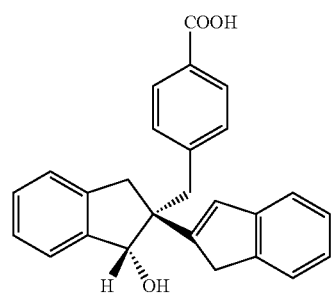

(II)

Also provided are pharmacologically acceptable salts of the compound of formula (II)—compound 2.

The active enantiomers have been characterised, spectroscopically, by their physical and chemical properties and by normal and chiral HPLC retention data.

A specific enantiomeric form has been found to be particularly useful for the treatment of IBD.

The invention also provides the N-Methyl-(D)-Glucamine salt of the compound of formula III:

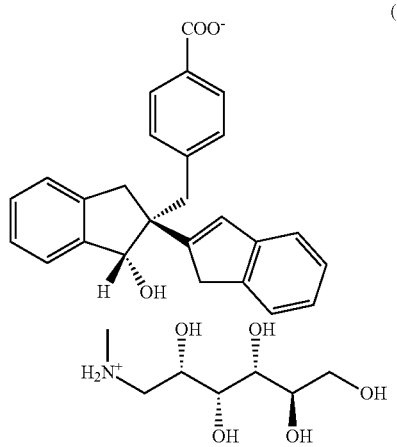

(III, compound 6)

The compounds of the invention may crystallize in more than one form. This characteristic is referred to as polymorphism, and such polymorphic forms ("polymorphs") are within the scope of the invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein are capable of existing as stereoisomers. The scope of the present invention includes mixtures of stereoisomers as well as purified or enriched mixtures. Also included within the scope of the invention are the individual isomers of the compounds of the invention as well as any wholly or partially equilibrated mixtures thereof. Certain compounds of the invention contain one or more chiral centers. Therefore the present invention includes racemates, purified enantiomers, and enantiomerically enriched mixtures of the compounds of the invention. The compounds of the present invention include racemic and chiral indane dimers.

Salts encompassed within the term pharmaceutically acceptable salts refer to non-toxic salts of the compounds of this invention. Salts of the compounds of the present invention may comprise acid addition salts.

The invention includes a solvate of any of the compounds of the invention. The term solvate refers to a complex of variable stoichiometry formed by a solute (in this invention, a compound of the invention, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

The invention includes a prodrug of any of the compounds of the invention. The term prodrug refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art.

The invention further provides a pharmaceutical composition comprising any of the compounds described above.

The active compound may be present in the medicament for use in man at a suitable dose to achieve the desired effect. For example, the final dose may be between 0.1 and 10 mg/kg.

It may be possible to administer the compounds of the invention in the form of a bulk active chemical. It is however, preferred that the compounds be administered in the form of a pharmaceutical formulation or composition. Such formulations may comprise one or more pharmaceutically acceptable excipient, carrier or diluent.

The compounds of the invention may be administered in a number of different ways. The compounds may be administered orally. Preferred pharmaceutical formulations for oral administration include tablets, capsules, caplets, solutions, suspensions or syrups.

The pharmaceutical formulations may be provided in a form for modified release such as a time release capsule or tablet.

The medicament may be administered orally, parenterally, intra-nasally, trans-cutaneously or by inhalation.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For oral administration in the form of a tablet or capsule, the active drug component can be combined with an oral, non-toxic pharmaceutically acceptable inert carrier such as ethanol, glycerol, water, and the like. Powders may be prepared by comminuting the compound to a suitable fine size and mixing with an appropriate pharmaceutical carrier such as an edible carbohydrate such as starch or mannitol. Flavorings, preservatives, dispersing agents, and coloring agents and the like may also be included.

Capsules may made by preparing a powder, liquid, or suspension mixture and encapsulating within gelatin or other suitable shell material. Lubricants such as colloidal silica, talc, magnesium stearate, calcium stearate, or solid polyethylene glycol may be added to the mixture. A disintegrating or solubilizing agent such as calcium carbonate or sodium carbonate can also be added to improve the availability of the medicament when the capsule is ingested. Other agents such as binders, lubricants, disintegrating agents, and coloring agents can also be incorporated into the mixture. Examples of suitable binders include starch, gelatin, natural sugars, corn sweeteners, natural and synthetic gums, tragacanth, or sodium alginate, carboxymethylcellulose, polyethylene glycol and the like. Suitable lubricants for these dosage forms include, for example, sodium oleate, sodium stearate, magnesium stearate, sodium benzoate, sodium acetate, sodium chloride, and the like. Suitabel disintegrators include, without limitation, starch, methyl cellulose, agar, bentonite, xanthan gum, and the like.

Tablets may be formulated by preparing a powder mixture, granulating the mixture, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or the like. The powder mixture can be wet-granulated with a binder such as syrup, starch paste, or solutions of cellulosic or polymeric materials, and pressing through a screen.

The compounds of the present invention can also be combined with a free flowing inert carrier and compressed into tablets directly without going through other steps such as granulating. A clear or opaque protective coating consisting of a sealing coat of a suitable material such as shellac, sugar or polymeric material, and a polish coating for example of wax can be provided. If appropriate colourants be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle.

Suspensions can be formulated by dispersing the compound in a non-toxic vehicle. Solubilisers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in suitable polymers, wax, or the like.

The compounds described herein and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the invention and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include, for example, polyvinylpyrrolidone (PVP). The compounds may also be coupled to a biodegradable polymer achieve controlled release of a drug. Such polymers include polylactic acid, polycyanoacrylates, and block copolymers of hydrogels.

Pharmaceutical formulations adapted for transdermal administration may be presented as discrete patches intended to remain in intimate contact with the skin/epidermis of a patient for a prolonged period of time. For example, the active ingredient may be delivered from the patch by iontophoresis.

Pharmaceutical formulations adapted for topical administration may be formulated as ointments, creams, suspensions, lotions, powders, solutions, pastes, gels, sprays, aerosols, or oils. For treatments of external tissues the formulations may be applied as a topical ointment or cream.

For topical administration in the mouth the formulation may include lozenges, pastilles, and mouthwashes.

For nasal administration, a powder having a particle size for example in the range 20 to 500 microns may be used. The powder may be administered by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of metered dose pressurized aerosols, nebulizers, or insufflators and the like.

For rectal administration the formulation may be presented as suppositories or as enemas.

For vaginal administration the formulation may be in the form of pessaries, tampons, creams, gels, sprays or the like.

For parenteral administration the formulation may be aqueous and non-aqueous sterile injection solutions which may contain various additives such as anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and the like.

The compounds of the present invention and their salts, solvates, and physiologically functional derivatives thereof, may be employed alone or in combination with other therapeutic agents. The compound of the invention and the other pharmaceutically active agent(s) may be administered together or separately. If administered separately, administration may occur simultaneously or sequentially, in any order. The amounts of the compound of the invention and the other pharmaceutically active agent(s) and the relative timings of administration will be selected in order to achieve the desired combined therapeutic effect. The administration in combination of a compound of the invention salts, solvates, or physiologically functional derivatives thereof with other treatment agents may be in combination by administration concomitantly in either a single pharmaceutical composition including both compound or in separate pharmaceutical compositions each including one of the compounds. In some cases the combination of drugs may be administered separately in a sequential manner in which one agent is administered first and a second agent is administered second or the other way around. Such administration may be in a similar time frame or over longer time.

BRIEF DESCRIPTION OF THE DRAWINGS

The invention will be more clearly understood from the following description thereof given by way of example only, in which.

DETAILED DESCRIPTION OF THE INVENTION

Compound 1 represents a pair of diastereoisomers that result from the reduction and demethylation of the ketone compound A which has a chiral centre at C-2, and is, as a result, a pair of enantiomers.

Compound A

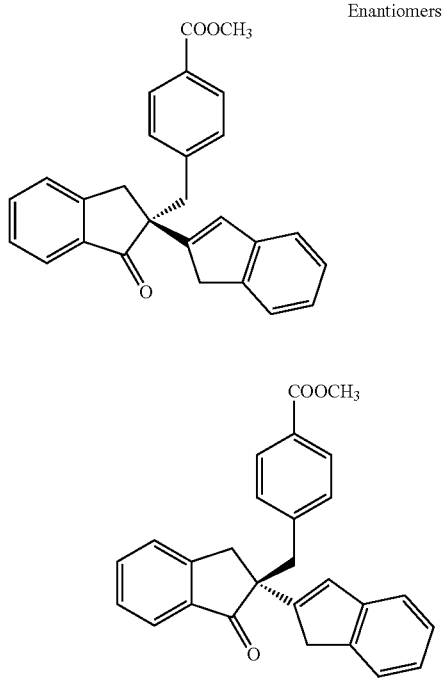

Enantiomers of compound A

Reduction of this compound with LiAlH$_4$ yields a compound of the formula

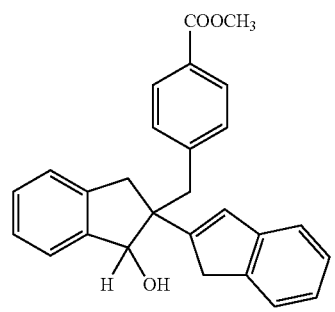 [SMILES: COC(=O)c1ccc(CC2(C3=Cc4ccccc4C3)Cc3ccccc3C2O)cc1]

This compound comprises two diastereoisomers:

Diastereoisomer B

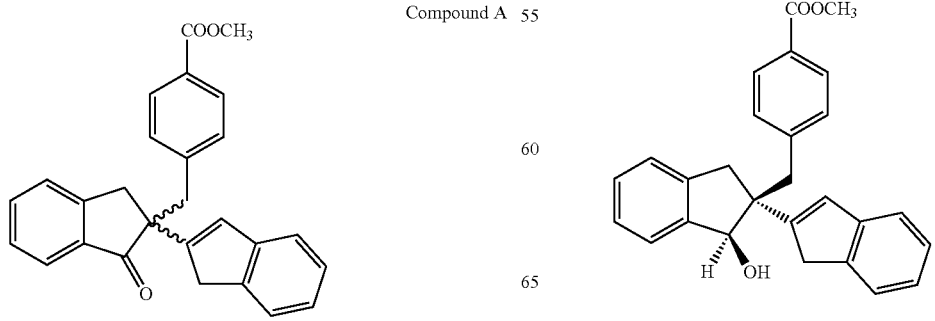

Diastereoisomer C

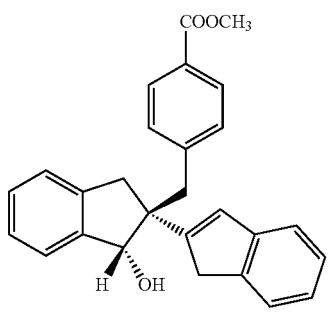

Hydrolysis of Diastereoisomer B gives rise to compounds 2 and 3

Compound 2

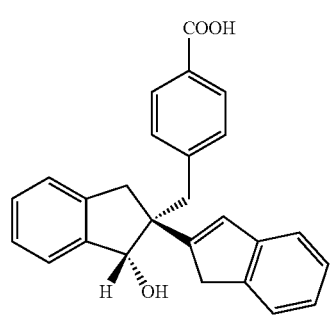

Compound 3

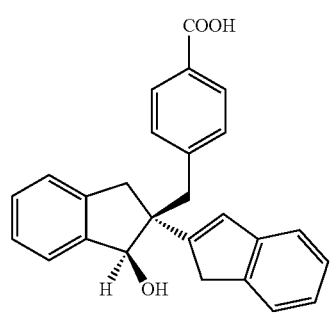

Hydrolysis of Diastereoisomer C gives rise to compounds 4 and 5.

Compound 4

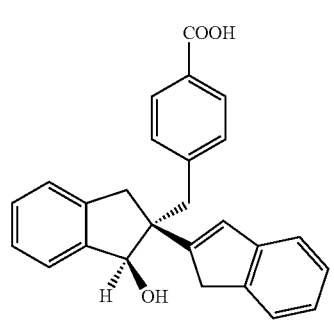

Compound 5

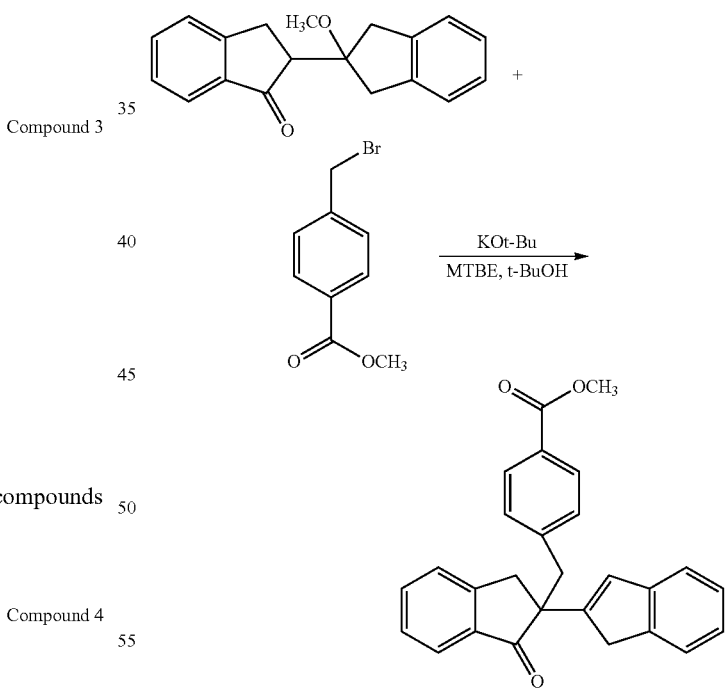

The diastereoisomers can be resolved chemically or chromatographically into their constituent enantiomers.

Figure 1:
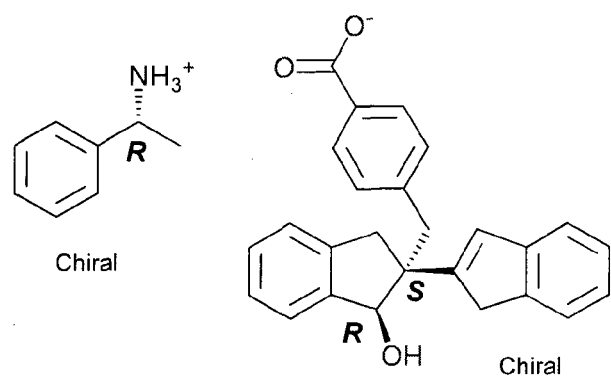
FIG. 1 is the X-ray crystal structure showing the absolute stereochemistry for the enantiomer compound 4 (R)-(+)-methylbenzylamine salt (compound 9)
Figure 1:
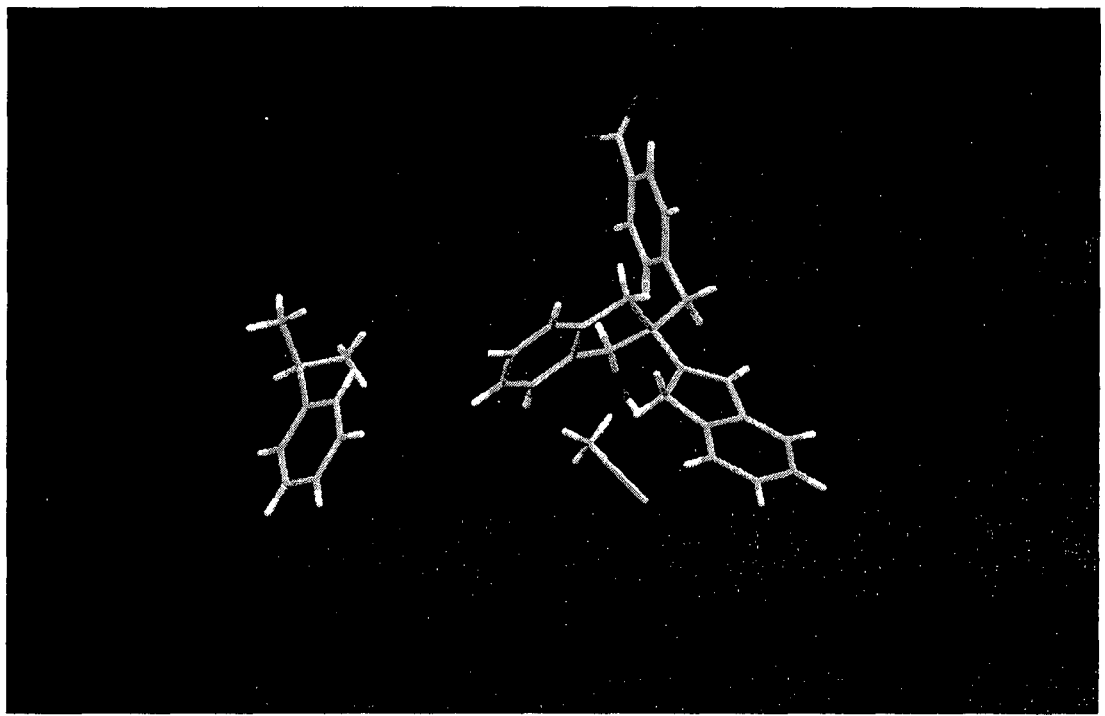

The absolute stereochemistry of compound 4 has been established by single crystal X-ray of compound 4 (R)-(+)-methylbenzylamine salt (compound 9) (FIG. 1).

Figure 2:
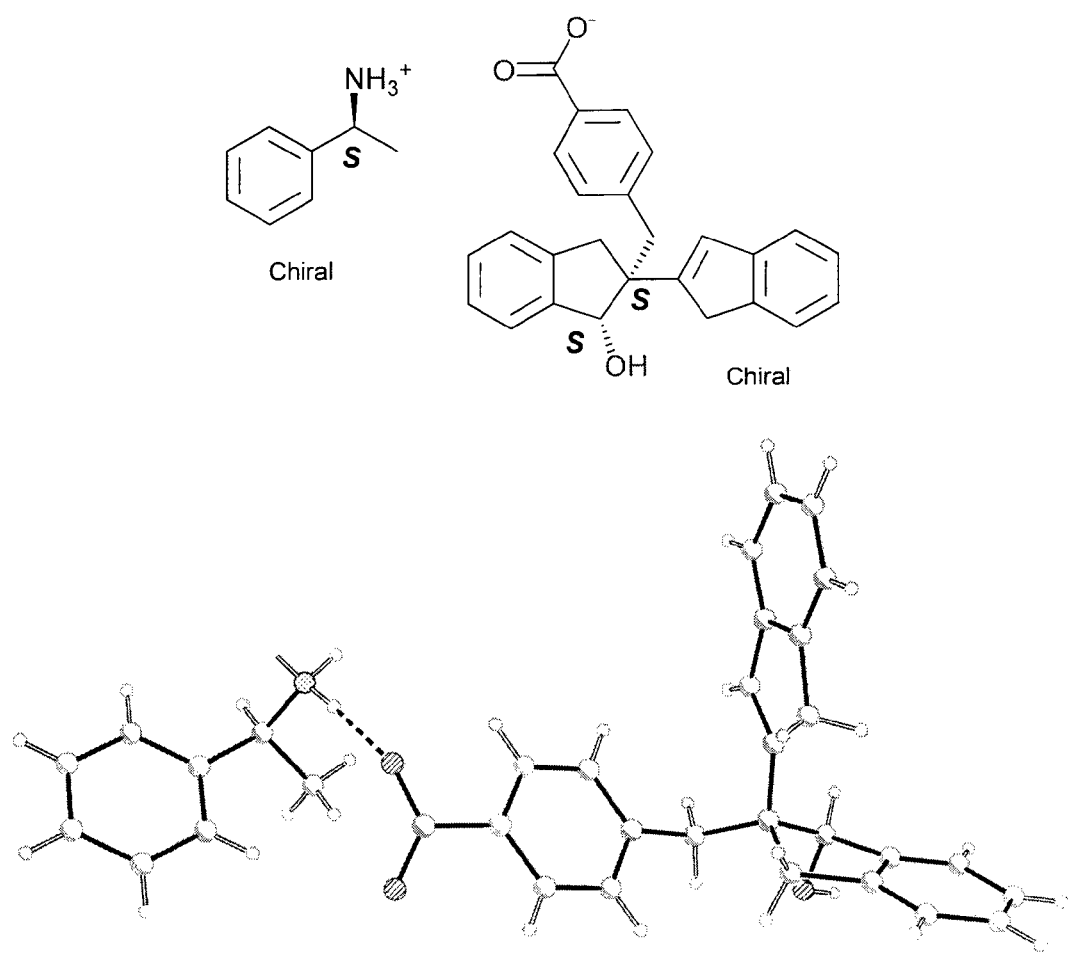
FIG. 2 is the X-ray crystal structure showing the absolute stereochemistry for the enantiomer compound 2 (S)-(−)-methylbenzylamine salt (compound 8)
Figure 2A:
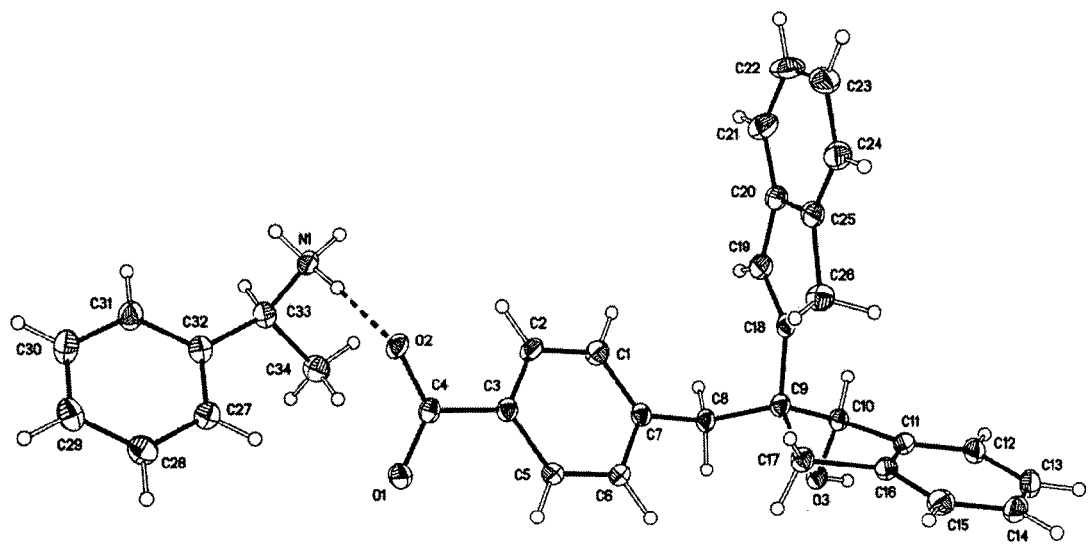
FIG. 2A is a view of a molecule of compound 8 from the crystal structure showing the numbering scheme employed. Anisotropic atomic displacement ellipsoids for the non-hydrogen atoms are shown at the 50% probability level. Hydrogen atoms are displayed with an arbitrarily small radius. Only the major disorder component is shown.

The absolute stereochemistry of compound 2 was confirmed by single crystal X-ray of compound 2 (S)-(−)-methylbenzylamine salt (compound 8) (FIGS. 2 and 2A).

General Reaction Procedures

General synthetic procedures for the coupling of enantiomeric mixtures as exemplified below are described in WO9720806A, the entire contents of which are herein incorporated by reference.

General Preparation of Acid Derivative Compound A

To a stirred solution of the coupled product (4 mmol, 1.00 g) in tert-butanol (5 mL) and diethyl ether (30 mL) under nitrogen was added methyl (4-bromomethyl)benzoate (6 mmol, 1.41 g). To this was added a solution of potassium tert-butoxide in tert-butanol (30 mL) and diethyl ether (5 mL), slowly drop wise. With each drop, the mixture turned a yellow colour and it then reverted to its original grey colour. The mixture was stirred for a further 3 hours until the TLC (80:20, hexane:ethyl acetate) showed no more starting material. The reaction was quenched by the addition of sat. NH₄Cl. The layers were separated and the aqueous layer extracted with diethyl ether (2×120 mL). The combined organic layers were washed with water, brine, dried over MgSO₄ and evaporated. The solid product precipitated from the crude on removal of most of the solvent. This was filtered off and washed with cold diethyl ether to give 0.98 g (62%) of a cream solid.

Reduction of Methyl Benzoate Compound

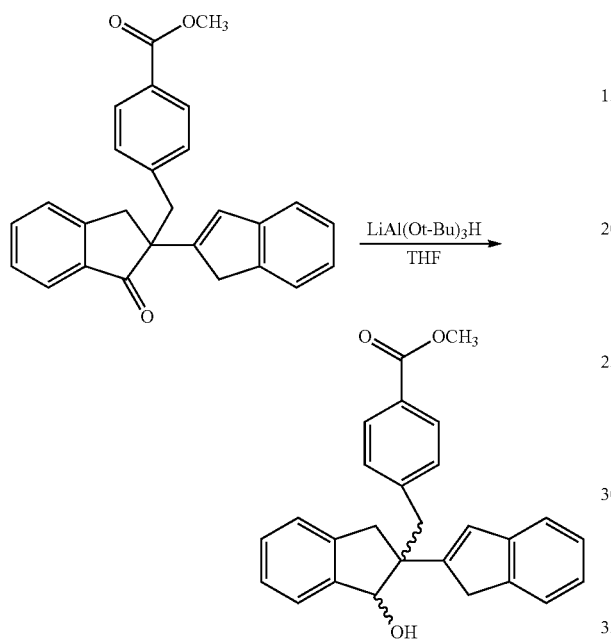

To a stirred solution of the methyl benzoate compound (1.27 mmol; 0.50 g) in THF (15 mL) was added lithium tri-tert-butoxyaluminohydride (1.9 mmol, 0.48 g), slowly portion wise. The reaction was monitored by TLC (80:20, hexane:ethyl acetate) and after 3 h, all of the starting material had been consumed.

The reaction was quenched by pouring onto ice and the crude product extracted into ethyl acetate by stirring the aqueous mixture for 10-15 min with ethyl acetate then pouring into a separatory funnel and then allowing it to separate. The combined organic layers were washed with water, brine, dried over MgSO₄ and evaporated to give 0.34 g (68%) of a cream-tan solid. The product was isolated as a mixture of two diastereoisomers in an approximately 2:1 ratio.

Analytical Results for the Mixture of Two Diastereoisomers

Purity (HPLC): 94.9% (as a 2:1 ratio of diastereoisomers)

$\delta_H$(300 MHz, CDCl₃): 2.77-3.60 (6H, m, 3×C$\underline{H}_2$) 3.85 (3H, s, C$\underline{H}_3$), [5.02 (1H, s, C$\underline{H}$—OH)] 5.18 (1H, s, C$\underline{H}$—OH), [6.23 (1H, s, C$\underline{H}$=C] 6.43 (1H, s, C$\underline{H}$=C), 6.90-6.98 (2H, m, Ar—$\underline{H}$), 7.11-7.21 (1H, m, Ar—$\underline{H}$), 7.22-7.31 (5H, m, Ar—$\underline{H}$), 7.36-7.42 (2H, m, Ar—$\underline{H}$), 7.78-7.84 (2H, m, Ar—$\underline{H}$).

Where possible, the value for the minor diastereoisomer is given in brackets.

$\delta_C$(75.5 MHz, CDCl₃): 38.3 (C$\underline{H}_2$), 38.4 (C$\underline{H}_2$), 38.6 (C$\underline{H}_2$), 39.9 (C$\underline{H}_2$), 40.3 (C$\underline{H}_2$), 43.4 (C$\underline{H}_2$), 51.9 (COO C$\underline{H}_3$), 52.0 (COOC$\underline{H}_3$), 55.9 (quat. $\underline{C}$), 56.3 (quat. $\underline{C}$), 82.0 (C$\underline{H}$—OH), 82.8 (C$\underline{H}$—OH), 120.5 (tert. $\underline{C}$), 120.7 (tert. $\underline{C}$), 123.5 (tert. $\underline{C}$), 123.6 (tert. $\underline{C}$), 124.0 (tert. $\underline{C}$), 124.2 (tert. $\underline{C}$), 124.5 (tert. $\underline{C}$), 124.6 (tert. $\underline{C}$), 124.8 (tert. $\underline{C}$), 124.9 (tert. $\underline{C}$), 125.1 (tert. $\underline{C}$), 125.2 (tert: $\underline{C}$), 126.1 (tert. $\underline{C}$), 126.4 (tert. $\underline{C}$), 127.0 (quat. $\underline{C}$), 127.1 (quat. $\underline{C}$), 128.0 (tert. $\underline{C}$), 128.2 (tert. $\underline{C}$), 128.5 (tert. $\underline{C}$), 128.8 (tert. $\underline{C}$), 129.0 (tert. $\underline{C}$), 129.2 (tert. $\underline{C}$), 129.5 (tert. $\underline{C}$), 2×130.0 (2×tert. $\underline{C}$), 2×130.2 (2×tert. $\underline{C}$), 130.7 (tert. $\underline{C}$), 140.4 (quat. $\underline{C}$), 141.5 (quat. $\underline{C}$), 142.8 (quat. $\underline{C}$), 143.2 (quat. $\underline{C}$), 143.5 (quat. $\underline{C}$), 143.6 (quat. $\underline{C}$), 143.7 (quat. $\underline{C}$), 144.2 (quat. $\underline{C}$), 144.3 (quat. $\underline{C}$), 144.5 (quat. $\underline{C}$), 150.4 (quat. $\underline{C}$), 152.6 (quat. $\underline{C}$), 167.0 ($\underline{C}$=O), 167.2 ($\underline{C}$=O).

Hydrolysis of Methyl Benzoate Moiety

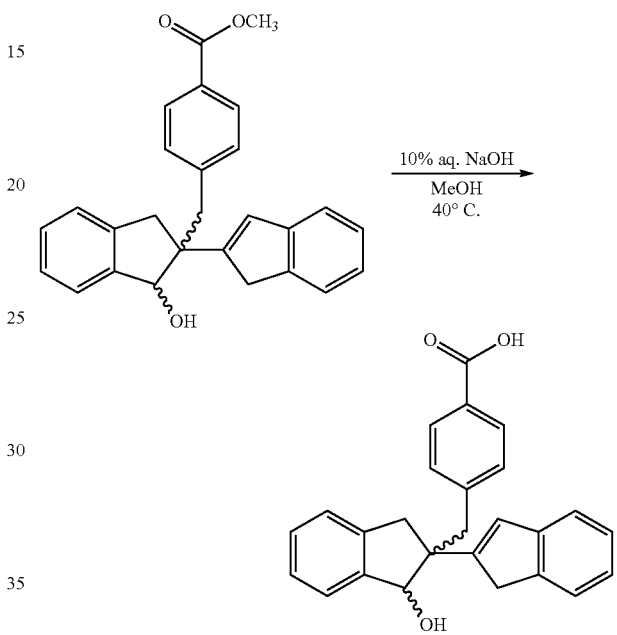

The ester was placed in a round-bottomed flask and 10% aq. NaOH (1 mL) was added to it followed by sufficient methanol to form a solution (6 mL). The solution was heated at 40° C. and monitored by TLC (80:20, hexane:ethyl acetate). After ca. 4 h, no further ester was seen.

The mixture was cooled and sat. NH₄Cl added (solution at pH 12). Dilute HCl was added to acidic pH (pH 2). The product was extracted from the cloudy solution into ethyl acetate (3×10 mL). The combined extracts were dried over MgSO₄ and evaporated in vacuo to give 0.15 g (quantitative) of a cream solid. The product was isolated as a mixture of two diastereoisomers in an approximately 2:1 ratio.

Analytical Results for the Mixture of Two Diastereoisomers

Purity (HPLC): 95.2% (as a 2:1 ratio of diastereoisomers)

$\delta_H$(400 MHz, CDCl₃): 2.81-3.59 (6H, m, 3×C$\underline{H}_2$), [5.05 (1H, s, C$\underline{H}$—OH)], 5.23 (1H, s, C$\underline{H}$—OH), 6.46 (1H, s, C$\underline{H}$=C), [6.66 (1H, s, C$\underline{H}$=C)], 6.95-7.03 (2H, m, Ar—$\underline{H}$), 7.12-7.17 (1H, m, Ar—$\underline{H}$), 7.21-7.29 (5H, m, Ar—$\underline{H}$), 7.37-7.43 (2H, m, Ar—$\underline{H}$), 7.85-7.91 (2H, m, Ar—$\underline{H}$).

Where possible, the value for the minor diastereoisomer is given in brackets.

$\delta_C$(100 MHz, CDCl₃): 37.9 (C$\underline{H}_2$), 38.1 (C$\underline{H}_2$), 38.2 (C$\underline{H}_2$), 39.5 (C$\underline{H}_2$), 39.9 (C$\underline{H}_2$), 43.1 (C$\underline{H}_2$), 55.5 (quat. $\underline{C}$), 55.9 (quat. $\underline{C}$), 81.6 (C$\underline{H}$—OH), 82.4 (C$\underline{H}$—OH), 120.2 (tert. $\underline{C}$), 120.3 (tert. $\underline{C}$), 123.1 (tert. $\underline{C}$), 123.2 (tert. $\underline{C}$), 123.5 (tert. $\underline{C}$), 123.9 (tert. $\underline{C}$), 124.1 (tert. $\underline{C}$), 124.4 (tert. $\underline{C}$), 124.5 (tert. $\underline{C}$), 124.7 (tert. $\underline{C}$), 125.9 (tert. $\underline{C}$), 126.0 (tert. $\underline{C}$), 126.5 (tert. $\underline{C}$), 2×126.7 (quat. $\underline{C}$ & tert. $\underline{C}$), 126.9 (quat. $\underline{C}$), 128.1 (tert. $\underline{C}$), 128.2 (tert. $\underline{C}$), 128.4 (tert. $\underline{C}$), 2×129.2 (2×tert. $\underline{C}$), 2×129.4 (2×tert. C), 2×129.8 (2×tert. C), 2×129.9 (2×tert. C), 130.4 (tert. C), 140.0 (quat. C), 141.0 (quat. C), 142.3 (quat. C), 142.7 (quat. C), 143.0 (quat. C), 143.2 (quat. C), 143.8 (quat. C), 144.0 (quat. C), 144.1 (quat. C), 144.7 (quat. C), 150.0 (quat. C), 152.0 (quat. C), 170.8 (C=O), 171.1 (C=O).

Chemical Separation of Enantiomers
Preparation of N—BOC D-phenylalanine derivative of methyl benzoate diastereoisomer and/or separation of subsequent diastereoisomers α1 and α2 (or β1 and β2)

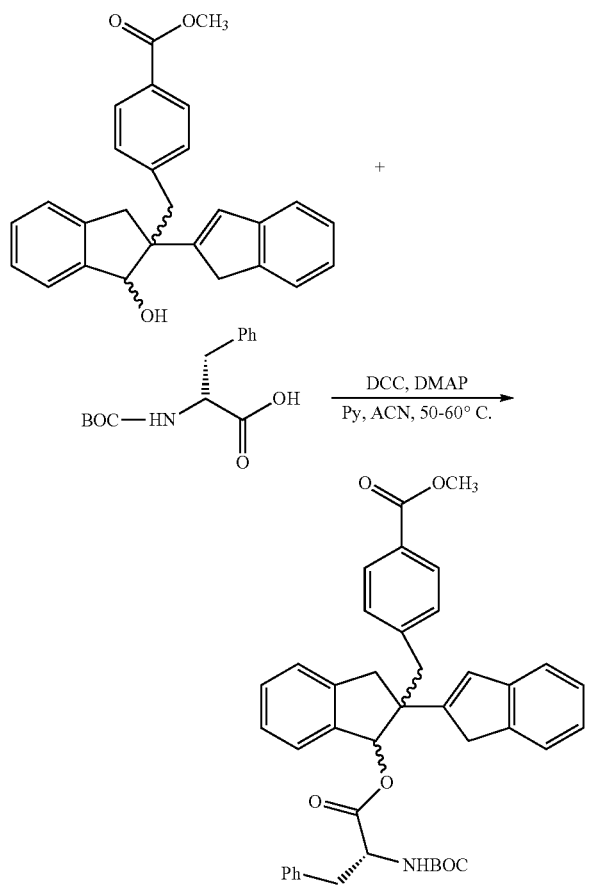

Note: procedure applicable to both diastereoisomers but the example given is for the first diastereoisomer.

Diastereoisomer A (2.5 mmol, 1.0 g) and N—BOC D-phenylalanine (3.1 mmol, 0.8 g) were placed in a round bottom flask fitted with a condenser and suspended in CH$_3$CN (25 mL) under nitrogen. To this suspension was added pyridine (3.1 mmol, 0.3 mL) followed by a solution of DCC (3.1 mmol, 0.7 g) and DMAP (10% mol, 0.25 mmol, 0.05 g) in CH$_3$CN (2 mL). The mixture was stirred for 20 h at 50° C., and then allowed to reach room temperature.

The white solid was filtered off and the solvent removed in vacuo. Ethyl acetate was added and the solution obtained was washed with 10% H$_2$SO$_4$, sat. NaHCO$_3$, dried over MgSO$_4$ and evaporated to give 2.1 g of a yellow oil (83% pure by HPLC, yield: quantitative).

The diastereoisomers α1 and α2 were separated by flash chromatography (90 g of silica/g of product) using hexane/MTBE 90:10. From 4.17 g of mixture, 1.3 g of α2, derivative was obtained (as well as 1.71 g of the α1 derivative and 0.3 g as a mixture of both).

Hydrolysis of N—BOC D-phenylalanine Derivative of Methyl Benzoate Compound (α1, α2, β1 or β2)

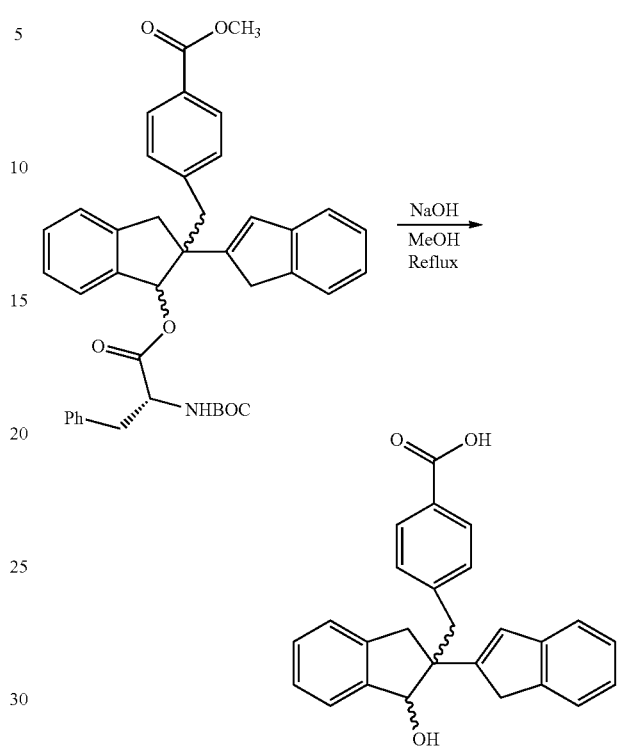

The diastereoisomer α2 (2.3 mmol, 1.45 g) was dissolved in methanol (25 mL) and NaOH (11.5 mmol, 0.45 g) was added and the mixture stirred at reflux temperature and monitored by TLC. After 20 h, the starting material was consumed.

The reaction was cooled to room temperature and quenched by addition of sat. NH$_4$Cl. The methanol was removed in vacuo and the aqueous solution acidified to pH 1 with conc. HCl. The product was extracted with ethyl acetate, dried over MgSO$_4$ and evaporated to give 1.6 g of a yellow gum, which was purified by a short silica column with hexane:MTBE 80:20 as eluent. 0.44 g of acid derivative compound 5 (50% yield) was obtained which was 97.2% pure by HPLC.

Note: An alternative hydrolysis was also carried out using 10% aqueous NaOH in methanol at 40-50° C. This procedure took almost 5 days to go to completion.

Analytical Results for Enantiomers α1, α2, β1, β2
Enantiomer β1 from Diastereoisomer B-Compound 3

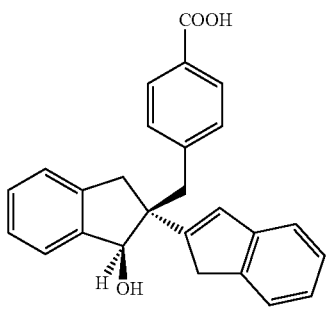 [SMILES: O=C(O)c1ccc(C[C@]2(C3=Cc4ccccc4C3)Cc3ccccc3[C@@H]2O)cc1]

Description: Cream amorphous solid

Melting point 195-196° C.

$[\alpha]_D$: +98.51 (1.07%, MeOH)

Purity: 99.0% $\delta_H$(400 MHz, CDCl$_3$): 2.87 (1H, d, J=13.28 Hz, C$\underline{H}_2$), 3.00-3.09 (2H, m, C$\underline{H}_2$), 3.29 (1H, d, J=13.36 Hz, C$\underline{H}_2$), 3.43-3.61 (2H, m, C$\underline{H}_2$), 5.27 (1H, s, C$\underline{H}$—OH), 6.49 (1H, s, C$\underline{H}$=C), 7.00 (2H, d, J=7.88 Hz, Ar—$\underline{H}$), 7.16-7.32 (6H, m, Ar—$\underline{H}$), 7.44 (2H, d, J=7.24 Hz, Ar—$\underline{H}$), 7.90 (2H, d, J=7.92 Hz, Ar—$\underline{H}$).

Enantiomer β2 from Diastereoisomer B—Compound 2

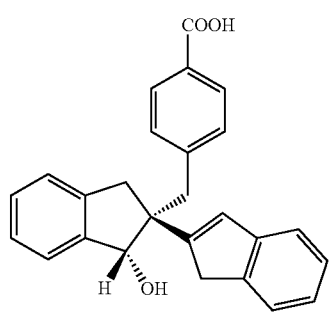 [SMILES: O=C(O)c1ccc(C[C@@]2(C3=Cc4ccccc4C3)Cc3ccccc3[C@H]2O)cc1]

Description: Cream amorphous solid

Melting point 184-185° C.

$[\alpha]_D$: −114.44 (0.18%, MeOH)

Purity: 99.8% $\delta_H$(400 MHz, CDCl$_3$): 2.87 (1H, d, J=13.32 Hz, C$\underline{H}_2$), 3.00-3.09 (2H, m, C$\underline{H}_2$), 3.29 (1H, d, J=13.28 Hz, C$\underline{H}_2$), 3.46 (1H, d, J=22.64 Hz, C$\underline{H}_2$), 3.58 (1H, d, J=22.56 Hz, C$\underline{H}_2$), 5.27 (1H, s, C$\underline{H}$—OH), 6.49 (1H, s, C$\underline{H}$=C), 7.00 (2H, d, J=8.04 Hz, Ar—$\underline{H}$), 7.15-7.34 (6H, m, Ar—$\underline{H}$), 7.44 (2H, d, J=7.20 Hz, Ar—$\underline{H}$), 7.90 (2H, d, J=8.04 Hz, Ar—$\underline{H}$).

Enantiomer α1 from Diastereoisomer C-Compound 4

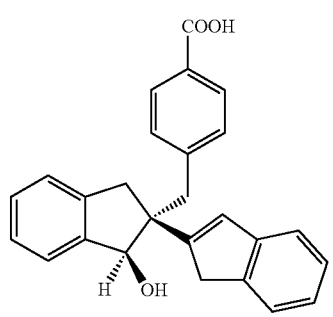 [SMILES: O=C(O)c1ccc(C[C@@]2(C3=Cc4ccccc4C3)Cc3ccccc3[C@@H]2O)cc1]

Description: Cream solid

Melting point 136-140° C.

$[\alpha]_D$: −39.3 (0.66%, MeOH)

Purity: 94.0%

$\delta_H$(400 MHz, CDCl$_3$): 2.90-3.59 (6H, m, 3×C$\underline{H}_2$), 5.08 (1H, s, C$\underline{H}$—OH), 6.70 (1H, s, C$\underline{H}$=C), 7.05 (2H, d, J=8.08 Hz, Ar—$\underline{H}$), 7.19 (1H, t, J=7.34 Hz, Ar—$\underline{H}$), 7.26-7.47 (7H, 2×m, Ar—$\underline{H}$), 7.93 (2H, d, J=8.08 Hz, Ar—$\underline{H}$).

Enantiomer α2 from Diastereoisomer C-Compound 5

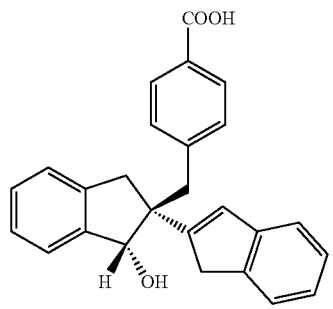 [SMILES: O=C(O)c1ccc(C[C@]2(C3=Cc4ccccc4C3)Cc3ccccc3[C@H]2O)cc1]

Description: Cream amorphous solid

Melting point 195-196° C.

$[\alpha]_D$: +32.1 (1.18%, MeOH)

Purity: 97.2%

$\delta_H$(400 MHz, CDCl$_3$): 2.94-3.59 (6H, m, 3×C$\underline{H}_2$), 5.08 (1H, s, C$\underline{H}$—OH), 6.70 (1H, s, C$\underline{H}$=C), 7.05 (2H, d, J=8.12 Hz, Ar—$\underline{H}$), 7.19 (1H, t, J=7.34 Hz, Ar—$\underline{H}$), 7.26-7.47 (7H, 2×m, Ar—$\underline{H}$), 7.93 (2H, d, J=8.12 Hz, Ar—$\underline{H}$).

HPLC Method

Achiral and Chiral HPLC methods were established for the qualitative and quantitative separation of enantiomers compounds 2, 3, 4, 5.

HPLC Resolution of Enantiomers

| Reverse phase method | |
| --- | --- |
| Column | Hypersil BDS C18, 5 μ, 250 × 4.6 mm |
| | Phenomenex Luna C18, 5μ, 250 × 4.6 mm, N: 32 |
| Wavelength | 210 nm |
| Flow rate | 1 mL/min (for ketone and esters) |
| | 0.6 mL/min (for acids and salts) |
| Mobile phase | 70:30 CH$_3$CN:0.1% aq. Acetic acid |
| Sample | 1 mg/mL, made up in mobile phase (or CH$_3$CN:dIW = 50:50 for acids/salts) |
| Retention times | Compound 1 - 20 min |
| | Diastereoisomers C (compounds 4/5) 9 min |
| | Diastereoisomers B (compounds 2/3) 10 min |
| Chiral method | |
| Column | ChiralPack IC, 5μ, 250 × 4.6 mm |
| Wavelength | 210 nm |
| Temperature | 25° C. |
| Flow rate | 0.35 mL/min |
| Mobile phase | n-Heptane/IPA/HOAc (or TFA) = 90/10/0.1 |
| Sample | 1 mg/mL, made up in mobile phase (or nHeptane/IPA/MeOH = 81/9/10 for salts) |
| Retention times | Compound A 54 min and >60 min |
| | Compound 4 - 30 min |
| | Compound 5 - 37 min |
| | Compound 3 - 18 min |
| | Compound 2 - 19 min |

Salt Formation

Salts were prepared by dissolving the free acid of compounds 2, 3, 4 and 5 in aqueous or aqueous organic solvent in the presence of the appropriate base and isolating the salt by evaporation of solvent.

Compound 6: The N-Methyl-(D)-Glucamine salt (NMDG) of compound 2.

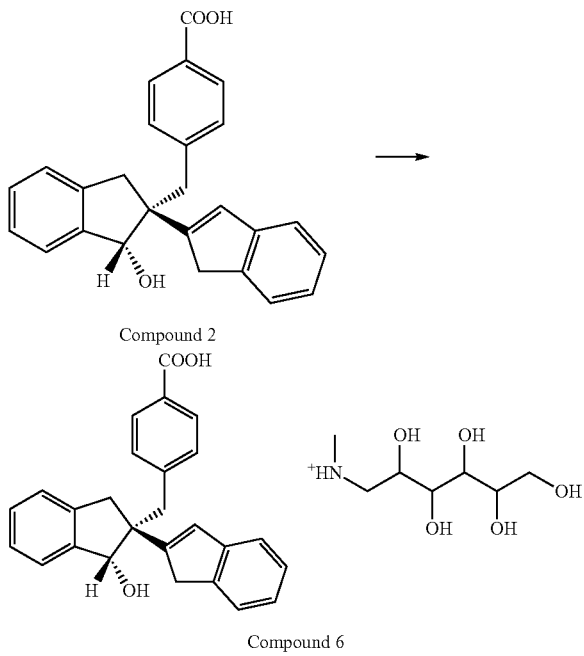

Compound 6 Physiochemical Properties:
Appearance: Off-white solid
Molecular Weight: 577 (free acid: 382)
Molecular Formula: $C_{33}H_{39}O_8N$ (free acid: $C_{26}H_{22}O_3$)
Melting Point: 165-167° C.
Compound 6: $[\alpha]_D$: −76.5 (sample concentration: 200 mg/10 ml in Water)
Mass (Da): ES+ only [NMDG+Na] was visible
Elemental analysis: Calc: C (68.61), H (6.80), N (2.42), O (22.16). Found: C (68.44), H (6.80), N (2.50), O (21.98).
$\delta_H$(400 MHz, DMSO): 2.48 (3H, apparent s, NC$\underline{H}_3$), 2.65 (1H, d, J=13.56 Hz, HC$\underline{H}$), 2.84-3.02 (4H, m), 3.16 (1H, d, J=13.60 Hz, HC$\underline{H}$), 3.40-3.70 (7H, m), 3.85-3.92 (1H, in), 5.06 (1H, s, C$\underline{H}$—OH), 5.93 (1H, broad s, CH—O$\underline{H}$), 6.41 (1H, s, C$\underline{H}$=C), 6.80 (2H, d, J=7.92 Hz, Ar—$\underline{H}$), 7.06-7.41 (8H, m, Ar—$\underline{H}$), 7.64 (2H, d, J=7.80 Hz, Ar—$\underline{H}$).
$\delta_C$(100 MHz, DMSO): 33.8 ($\underline{C}H_3$), 37.9 ($\underline{C}H_2$), 38.2 ($\underline{C}H_2$), 39.5 ($\underline{C}H_2$), 51.6 ($\underline{C}H_2$—N), 55.8 (quat. $\underline{C}$), 63.5 ($\underline{C}H_2$—O), 69.0 ($\underline{C}H$—O), 70.3 ($\underline{C}H$—O), 70.6 ($\underline{C}H$—O), 71.3 ($\underline{C}H$—O), 81.1 ($\underline{C}H$—OH), 120.1 (tert. $\underline{C}$), 123.4 (tert. $\underline{C}$), 123.7 (tert. $\underline{C}$), 124.3 (tert. $\underline{C}$), 124.4 (tert. $\underline{C}$), 126.1 (tert. $\underline{C}$), 126.3 (tert. $\underline{C}$), 127.0 (tert. $\underline{C}$), 127.5 (tert. $\underline{C}$), 2×128.5 (2×tert. $\underline{C}$), 2×129.1 (2×tert. $\underline{C}$), 140.4 (quat. $\underline{C}$), 141.1 (quat. $\underline{C}$), 142.9 (quat. $\underline{C}$), 144.5 (quat. $\underline{C}$), 145.2 (quat. $\underline{C}$), 154.3 (quat. $\underline{C}$), 170.4 ($\underline{C}$=O).

X-Ray Studies

The absolute stereochemistry of compound 2 was established by single crystal X-ray analysis of its (S)-(−)-methylbenzylamine salt (compound 8). The results are given in Appendix 2. The results were in agreement with the stereochemistry shown in FIG. 2. The absolute stereochemistry of compounds 4 and 5 were established by conversion of the alcohols (compounds 2-5) to their ketenes and by correlation of their optical rotations.

Inflammatory Bowel Disease (IBD)

Inflammatory Bowel Disease (IBD) consists of two idiopathic inflammatory diseases, Ulcerative Colitis (UC) and Crohn's Disease (CD). The greatest distinction between CD and UC is the range of inflamed bowel tissue. Inflammation in CD is discontinuously segmented, known as regional enteritis, while UC is superficial inflammation extending proximally and continuously from the rectum. At present the cause of IBD is unknown. The disease seems to be related to an exaggerated mucosal immune response to infection of the intestinal epithelium because of an imbalance of pro-inflammatory and immune-regulatory molecules. The inheritance of patterns of IBD, suggest a complex genetic component of pathogenesis that may consist of several combined genetic mutations. Currently no specific diagnosis exists for IBD, but as an understanding of pathogenesis improves so will testing methods. Treatment of IBD consists of inducing and maintaining remission. IBD patients may be maintained on remission by use of a 5-aminosalycilate. However, while the use of aminosalycilates in UC provides considerable benefit, both in inducing remission in mild to moderate disease and in preventing relapse, the usefulness of these drugs to maintain remission in CD is questionable and is no longer recommended. The mainstay of treatment of active disease is a corticosteroid, commonly used for limited periods to return both UC and CD patients to remission, though budesonide, designed for topical administration with limited systemic absorption, has no benefit in maintaining remission. Alternatives, such as the immunosuppressive drugs azathioprine and mercaptopurine, together with methotrexate and cyclosporine have limited efficacy and the capability of inducing grave adverse effects. Anti-TNFα antibodies such as infliximab and adalimubab may be used in those patients unresponsive to standard immunosuppressive therapy. However, many patients fail to respond to anti-TNFα therapy, either due to their particular phenotype or by the production of autoantibodies.

Acute Murine DSS Colitis Model

The dextran sodium sulphate (DSS) colitis model is an experimental mouse model that exhibits many of the symptoms observed in human UC, such as diarrhoea, bloody faeces, mucosal ulceration, shortening of the colon, weight loss and alterations in certain colon cytokines. The study is widely used as a model for studying the pathogenesis of UC and also for screening new therapeutic interventions for the treatment of UC.

In these studies, an acute colitis model was used, with 5% DSS administered in the drinking water of BALB/c mice. This dosage regime induces severe acute colitis, by days 7-8 mice had overt rectal bleeding and marked weight loss; unless sacrificed beforehand, all mice would have died by days 10-12.

Mice

Specific Pathogen-Free BALB/c mice, 6-8 weeks of age, were obtained from a commercial supplier (Harlan UK). Mice were fed irradiated diet and housed in individually ventilated cages (Tecniplast UK) under positive pressure.

DSS Treatment

DSS (5%) was dissolved in drinking water. Compounds were administered orally at a dose of 10 mg/kg or 30 mg/kg on days 0-7, and mice were culled on day 8 or day 9, depending on the severity of the disease. The mice were checked each day for morbidity and the weight of individual mice was recorded. Induction of colitis was determined upon autopsy, length of colon and histology. Colons were recovered and stored at −20° C. for immunological analysis. All of the compounds and experimental groups are randomly alphabetically labelled. Throughout experiments all data recording was performed in a blind manner. The codes on boxes/groups were not broken until after the data was analysed i.e. boxes labelled A, B, C etc were identified as untreated, DSS-treated, or DSS+compound-treated.

To quantify the extent of colitis, a disease activity index (DAI) was determined based on weight loss, faecal blood and stool consistency. A score was given for each parameter, with the sum of the scores used as the DAI. For each treatment group n=8.

Description of DAI

| Score | Weight loss % | Stool consistency | Faecal blood |
|---|---|---|---|
| 0 | None | Normal | None |
| 1 | 1-3 | | |
| 2 | 3-6 | Loose stool[1] | Visible in stool |
| 3 | 6-9 | | |

-continued

Description of DAI

| Score | Weight loss % | Stool consistency | Faecal blood |
|---|---|---|---|
| 4 | >9 | Diarrhea[2] | Gross bleeding[3] |

Definitions:
[1]Loose stool - stool not formed, but becomes a paste on handling.
[2]Diarrhea - no stool formation, fur stained around the anus.
[3]Gross bleeding - fresh blood on fur around the anus with excessive blood in the stool.

Administration of Compounds

All compounds were prepared for oral gavage (0.1 mL per os (p.o.) per 10 g body weight) as a suspension in 0.5% carboxymethyl cellulose/2% Tween 80, at a dose of 3-30 mg/Kg. Compounds as free acid were initially dissolved in absolute alcohol and diluted with 14+1 with 0.5% carboxymethyl cellulose/2% Tween 80; this resulted in a fine precipitate in suspension while N-Methyl-(D)-Glucamine salts were soluble in the vehicle alone.

Figure 3:
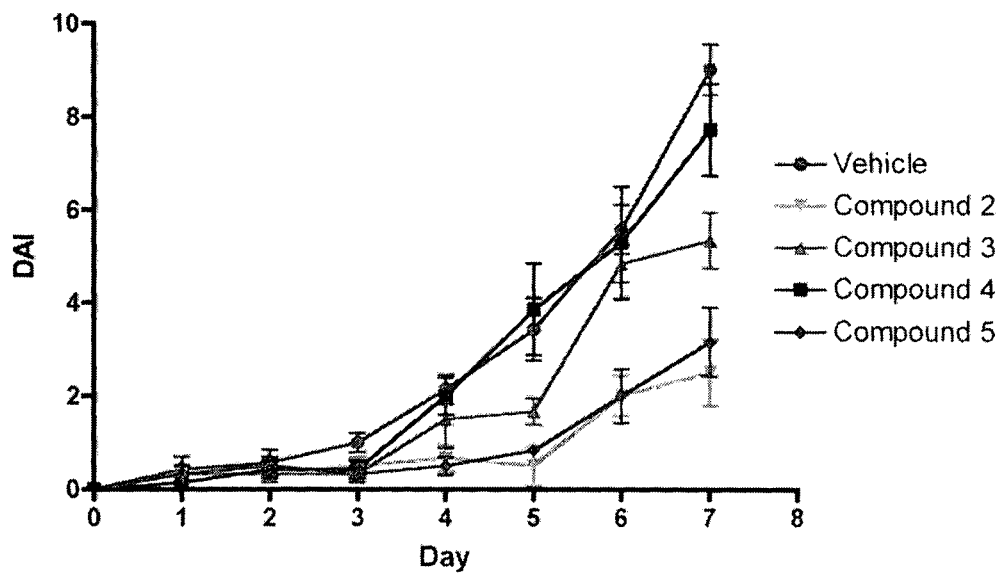
FIG. 3 is a graph of the effect of compounds 2, 3, 4 and 5 at 30 mg/kg on disease activity index (DAI) over 7 days in 5% DSS colitis.
Figure 4:
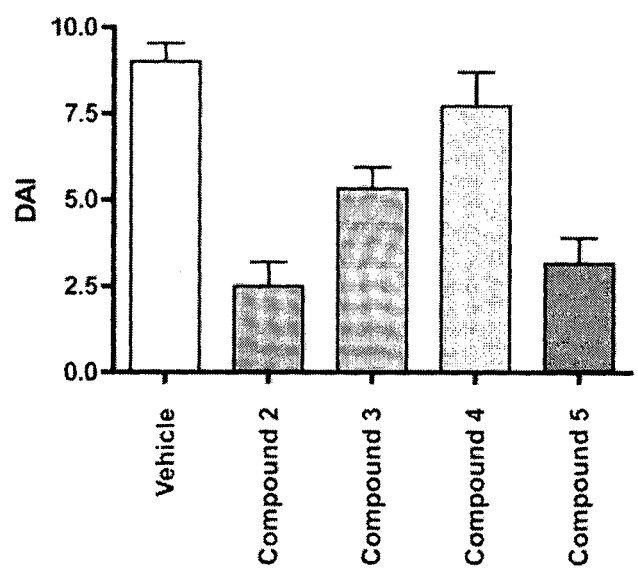
FIG. 4 is a bar chart of the effect of compounds 2, 3, 4 and 5 at 30 mg/kg on disease activity index (DAI) at day 7 in 5% DSS colitis.

Effect of Individual Enantiomers Compounds 2, 3, 4 and 5 in 5% DSS Murine Colitis BALB/c given 5% DSS in drinking water were administered compounds 2, 3, 4 and 5 at 30 mg/kg p.o. as a suspension in 0.5% carboxymethyl cellulose/2% Tween 80 daily for 7 days. DAI measures the extent of the disease in this model. Compound 4 was without activity on this variable, there not being any significant (P>0.05) difference in DAI at any time point (FIG. 3). At day 7, both compound 2 and compound 5 significantly (P<0.5) reduced DAI by a considerable margin, from 9.0+0.53 for vehicle controls to 3.2±0.73 for compound 5 and 2.5±0.71 for compound 2, there being no significant difference between the two (FIG. 4). In comparison, compound 3 reduced DAI to only 5.3±0.6. This was significantly (P>0.05) less potent than either compound 2 or compound 5. Further, while the DAI in compound 3-treated mice was statistically (P<0.05) less than vehicle controls at day 7 (FIG. 4), at day 6 there was no statistical (P>0.05) difference between compound 3 and vehicle (FIG. 3). In conclusion, of the four enantiomers, compounds 2, 3, 4 and 5 both compounds 2 and 5 are highly active in this model at 30 mg/kg. Compound 3 has minimal activity which is significantly (P<0.05) less than compound 2 and compound 5. Compound 4 is almost devoid of activity in this 5% DSS murine colitis model.

Selection of a Salt of Compounds 2 and 5

As a consequence of the limited aqueous solubility of the enantiomers compound 2 and compound 5, we attempted the synthesis of five salts of compound 5. The sodium salt, potassium salt, calcium salt, α-methylbenzylamine salt and N-Methyl-(D)-Glucamine salt were synthesised. The sodium and calcium salt were unsuccessful. The three salts of compound 5, named potassium salt, α-methylbenzylamine salt and N-Methyl-(D)-Glucamine salt were used for solubility and partition coefficient (log P) studies.

The solubility of the four compounds was determined:

| Compound | Milli-RO $H_2O$ µg/mL | pH 4.0 Buffer µg/mL | pH 7.0 Buffer µg/mL | pH 9.0 Buffer µg/mL |
|---|---|---|---|---|
| Compound 5 | 1.38 | 0.33 | 320.1 | 369.6 |
| Compound 5 Potassium salt | 217.0 | 0.15 | 54.71 | 340.3 |
| Compound 5 Methyl-benzylamine salt | 413.9 | 0.20 | 227.4 | 311.0 |
| Compound 5 N-Methyl-D-Glucamine salt | >60,000* | 0.14 | >60,000* | >60,000* |

*Estimated value

Compound 5 N-Methyl-(D)-Glucamine salt (compound 7) was determined, surprisingly, to be the most soluble compound from this group of analogous compounds by a considerable margin, with a solubility of >60,000 µg/mL in Milli-RO water, 0.14 µg/mL in pH 4 buffer, >60,000 µg/mL in pH 7.0 and >3,000 µg/mL in pH 9.0 buffer. Almost identical values were obtained with compound 2 N-Methyl-(D)-Glucamine (compound 6) with a solubility of >60,000 µg/mL in Milli-RO water, 0.5 µg/mL in pH4 buffer, >60,000 µg/mL in pH 7.0 and >3,000 µg/mL in pH 9.0 and buffer.

The partition coefficient of compound 5 and related analogous compounds was investigated using the HPLC method (reverse phase C18 HPLC column) at neutral, acidic and alkaline pH.

The partition coefficient of the four compounds was determined:

| Compound | Neutral Log10 POW | Basic Log10 POW | Acid Log10 POW |
|---|---|---|---|
| Compound 5 | 3.7 | 3.7 | 3.9 |
| Compound 5 Potassium salt | 3.7 | 3.7 | 3.9 |
| Compound 5 Methyl-benzylamine salt | 3.6 | 3.6 | 3.9 |
| Compound 5 N-Methyl-D-Glucamine salt | 3.5 | 3.5 | 3.8 |

The partition coefficient of each salt of compound 5 was found to be similar. It is suggested that this is happening because when the salt is in solution the compound dissociates into the parent compound 5 and the associated salt ion. As a result of this the measured partition coefficient was from the parent ion rather than the salt molecules.

The partition coefficient (Log 10 POW) of compound 2 N-Methyl-D-Glucamine salt (compound 6) was successfully determined in neutral, basic and acidic conditions as 3.5, 4.3 and 2.6 respectively.

N-Methyl-(D)-Glucamine was chosen as the salt candidate for both compound 2 and compound 5.

Figure 5:
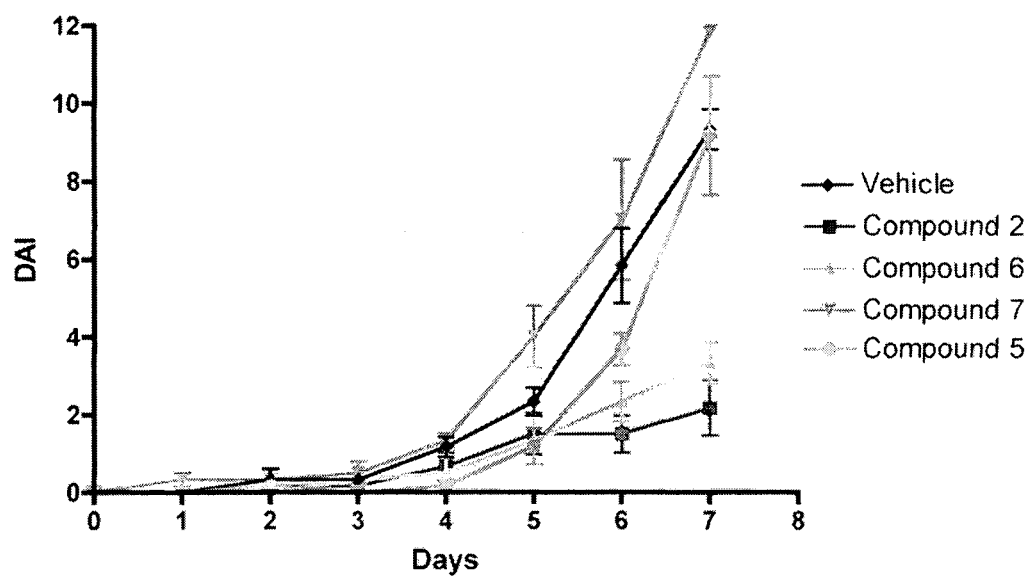
FIG. 5 is a graph of the effect of compounds 5, 7, 2 and 6 at 10 mg/kg on disease activity index (DAI) over 7 days in 5% DSS colitis.
Figure 6:
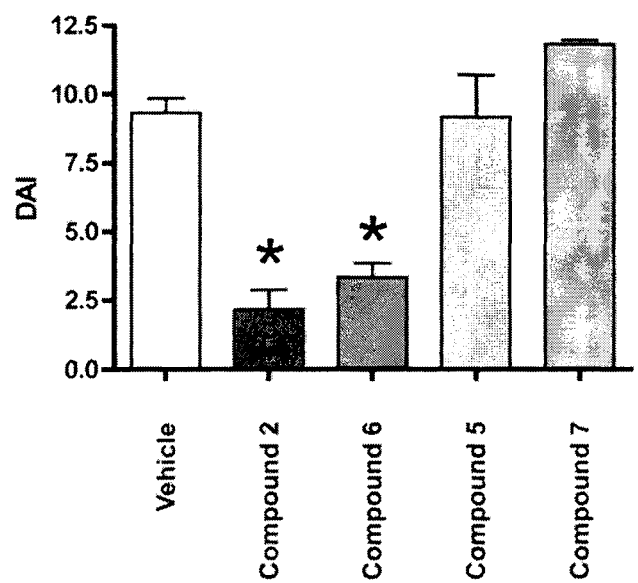
FIG. 6 is a bar chart of the effect of compounds 5, 7, 2 and 6 at 10 mg/kg on disease activity index (DAI) at day 7 in 5% DSS colitis. Asterisks indicate a significant ($P<0.05$) difference (1 way ANOVA) from the vehicle control group.

Effect of Enantiomers Compound 2 and Compound 5 and their N-Methyl-(D)-Glucamine Salts (Compounds 6 and 7) at 10 mg/kg in 5% DSS Murine Colitis Given that both compounds 2 and 5 show considerable activity in the 5% DSS model at 30 mg/kg, we then re-examined their activity, together with their N-Methyl-(D)-Glucamine salts at the lower dose of 10 mg/kg, given daily for 7 days as a suspension or solution in 0.5% carboxymethyl cellulose/2% Tween 80. No adjustment was made in the dosages of the salts to compensate for their increased molecular weight. Both compounds 5 and 7, at 10 mg/kg, had no significant (P>0.05) effect on DAI in the 5% DSS murine colitis model when compared to vehicle control (see FIG. 5). In contrast, at day 7, both compound 2 and compound 6, the N-Methyl-(D)-Glucamine salt, at 10 mg/kg significantly (P<0.05) and potently reduced DAI from 9.3±0.51 (vehicle) to 2.1±0.7 and 3.3±0.52 respectively (FIG. 6).

In conclusion, compound 2 (and its N-Methyl-(D)-Glucamine salt, compound 6) is the most potent of the four enantiomers by a considerable margin, and the only enantiomer to retain activity at the lower dose level of 10 mg/kg.

Effect of a Range of Doses of Compound 6 and a Comparison with Prednisolone on 5% DSS Murine Colitis Compound 6 was selected as the most favoured enantiomer. The activity of compound 6 in the 5% DSS murine model of colitis at varying dose levels was tested to ascertain if there was a dose/response relationship and to make a comparison with a potent oral steroid, Prednisolone, commonly used to return patients suffering from acute exacerbations of IBD to remission.

Figure 7:
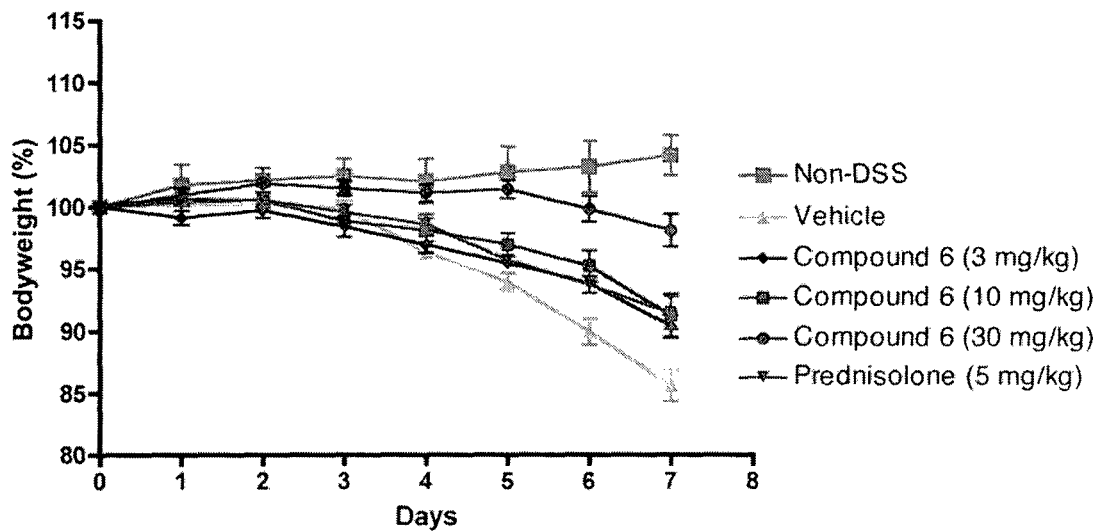
FIG. 7 Is a graph showing the effect of compound 6 on weight loss in 5% DSS-treated mice. Data are Mean±SEM from 6-7 mice per group.
Figure 8:
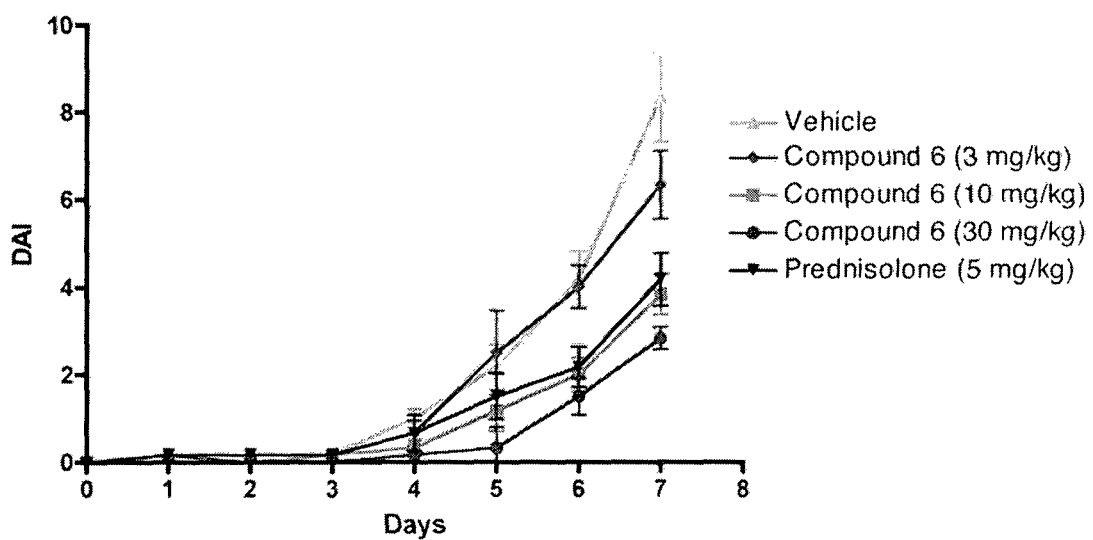
FIG. 8 Is a graph showing the effect of compound 6 on DAI in 5% DSS-treated mice. Data are Mean±SEM from 6-7 mice per group.

Mice were administered compound 6 at dose levels 3, 10 and 30 mg/Kg (equivalent to 6.6-20 mg/Kg of the compound 2). A group of DSS-treated mice was also treated with prednisolone, 5 mg/Kg. Prednisolone is a corticosteroid in clinical use in the treatment of human IBD and the quantity used in this study is the optimal dose of prednisolone for this model. After 3 days of treatment of BALB/c mice with 5% DSS in the drinking water signs of colitis were apparent. This was manifested as weight loss (FIG. 7) and an increase in the disease DAI (FIG. 8). However, following oral administration daily for 7 days, compound 6 at three doses (3, 10 and 30 mg/Kg) caused no overt reactions in mice. Compound 6 ameliorated the severity of colitis following acute DSS treatment in multiple parameters of disease examined. The capacity of compound 6 to ameliorate disease in the DSS model was dose-dependent. Compound 6 at 30 mg/Kg was therapeutic in the DSS model at a comparable, or better, efficacy relative to prednisolone at 5 mg/Kg.

Figure 9:
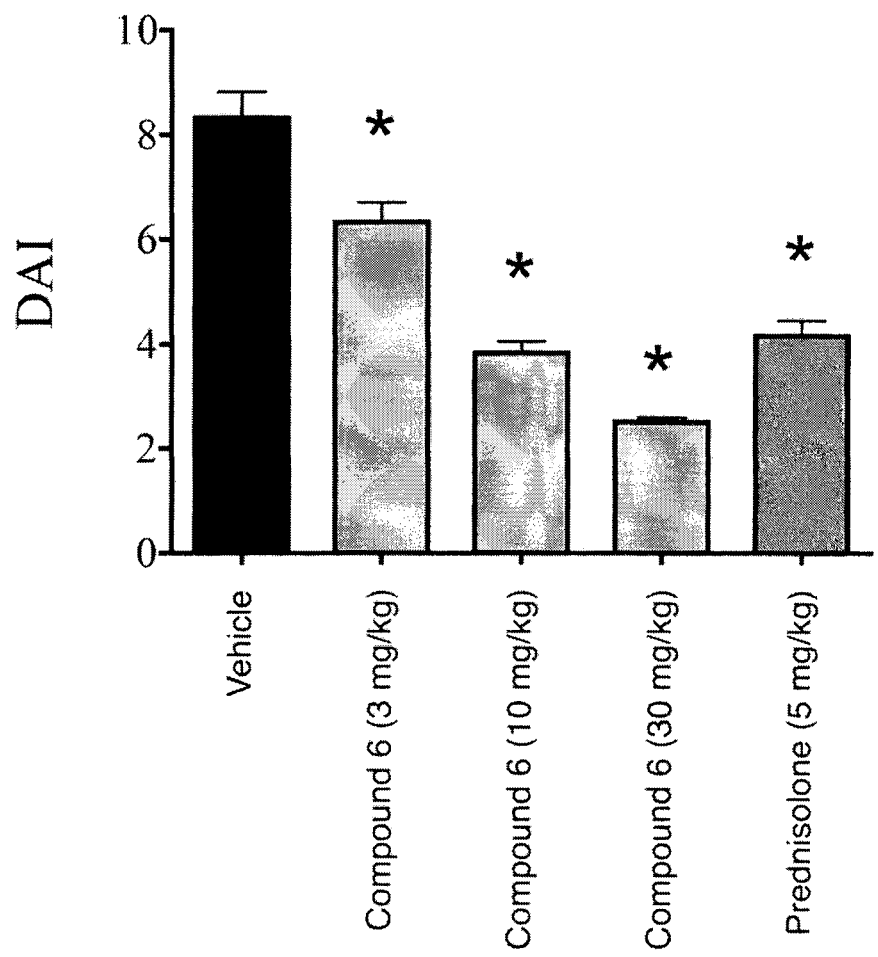
FIG. 9 Is a bar chart showing the effect of compound 6 on DAI in 5% DSS-treated mice on day 7. Data are Mean±SEM. Asterisks indicate a significant ($P<0.05$) difference (1 way ANOVA) from the vehicle control group.

The severity of these symptoms are progressive; by day 7 the DSS-treated mice have lost up to 15% of their body weight and all mice have perfuse rectal bleeding. The DAI values on the day of autopsy showed that mice treated with compound 6 3-30 mg/kg had at each dose level, a significantly (P<0.05–P<0.01) lower DAI than vehicle controls. Prednisolone (5 mg/kg) also significantly (P<0.01; ANOVA; Dunnett Multiple Comparison Test), reduced DAI scores (FIG. 9).

Figure 10:
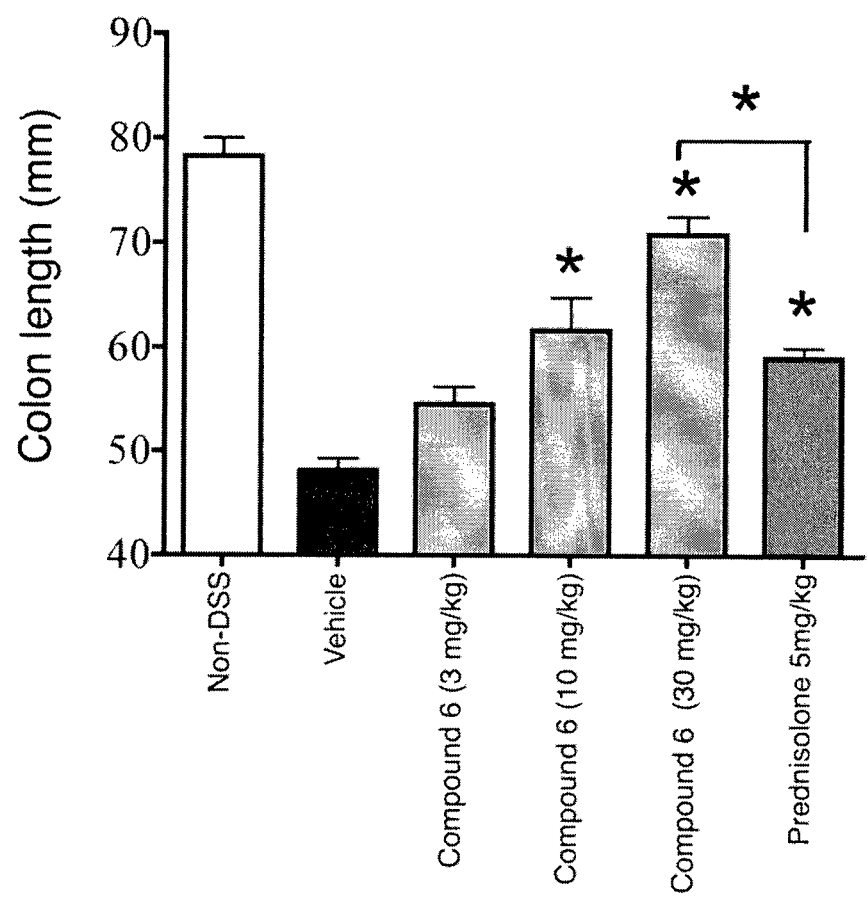
FIG. 10 Is a bar chart showing the effect of compound 6 on Colon length of 5% DSS-treated mice on day 7. Asterisks indicate a significant (P<0.05) difference (1 way ANOVA) from the vehicle control group.

At autopsy on day 7, there was significant shortening of colon length (P<0.05–P<0.01; ANOVA; Dunnett Multiple Comparison Test) in all DSS treated groups compared to colons from mice not treated with DSS (FIG. 10). The lowest dose of 3 mg/kg of compound 6 did not have a significant effect in inhibiting colon shortening when compared to vehicle controls whereas the 10 and 30 mg/kg groups and the Prednisolone group did have a significant effect. Compound 6 at 30 mg/kg was significantly better than Prednisolone (P<0.05; ANOVA; Dunnett Multiple Comparison Test) (FIG. 10).

Figure 11:
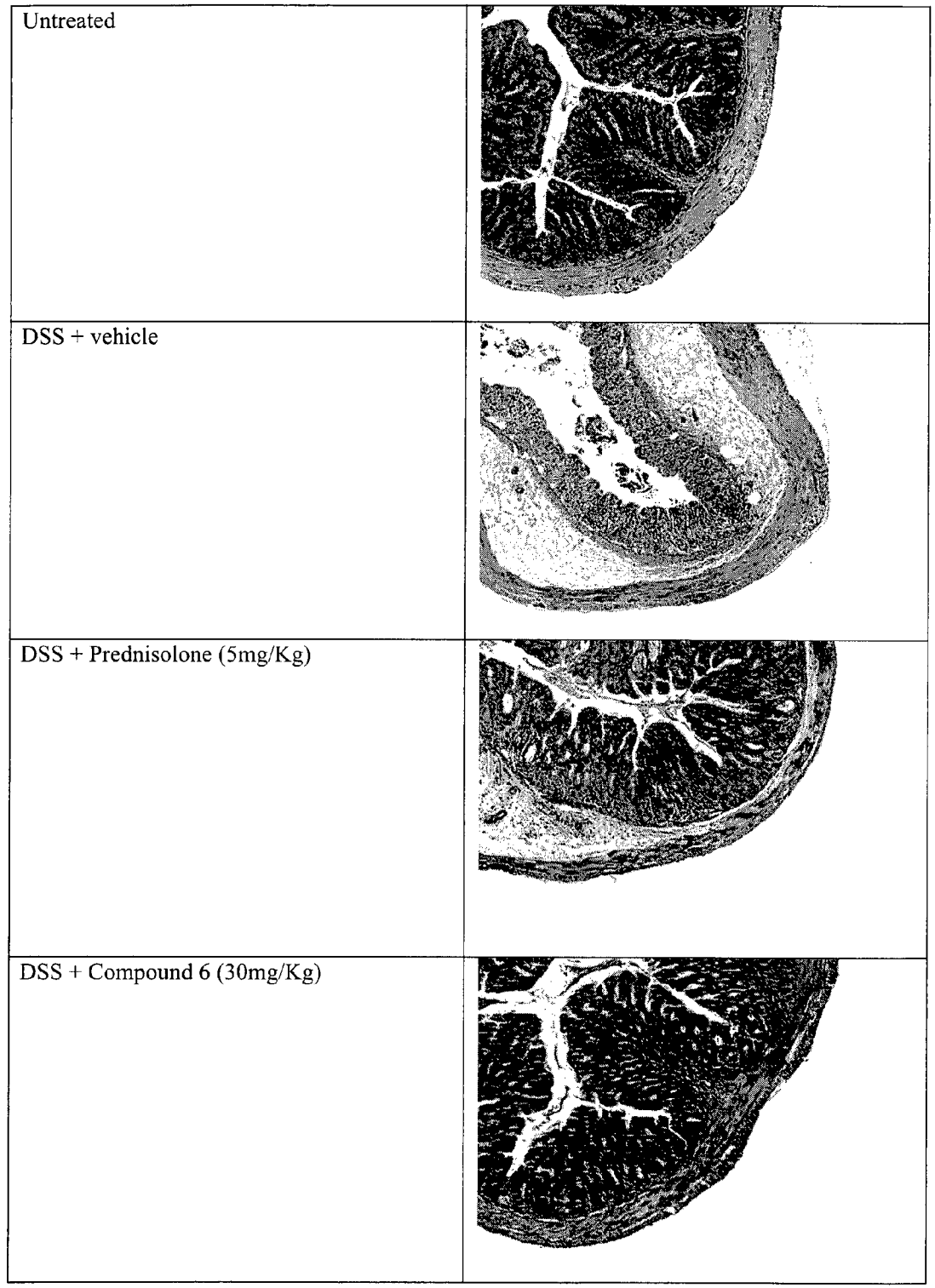
FIG. 11 Shows representative haematoxylin and eosin-stained sections from distal colons of mice. Higher magnifications (×10) are shown.

Following DSS treatment histology sections of the distal colon showed extensive crypt damage and cell infiltration (FIG. 11).

Figure 12:
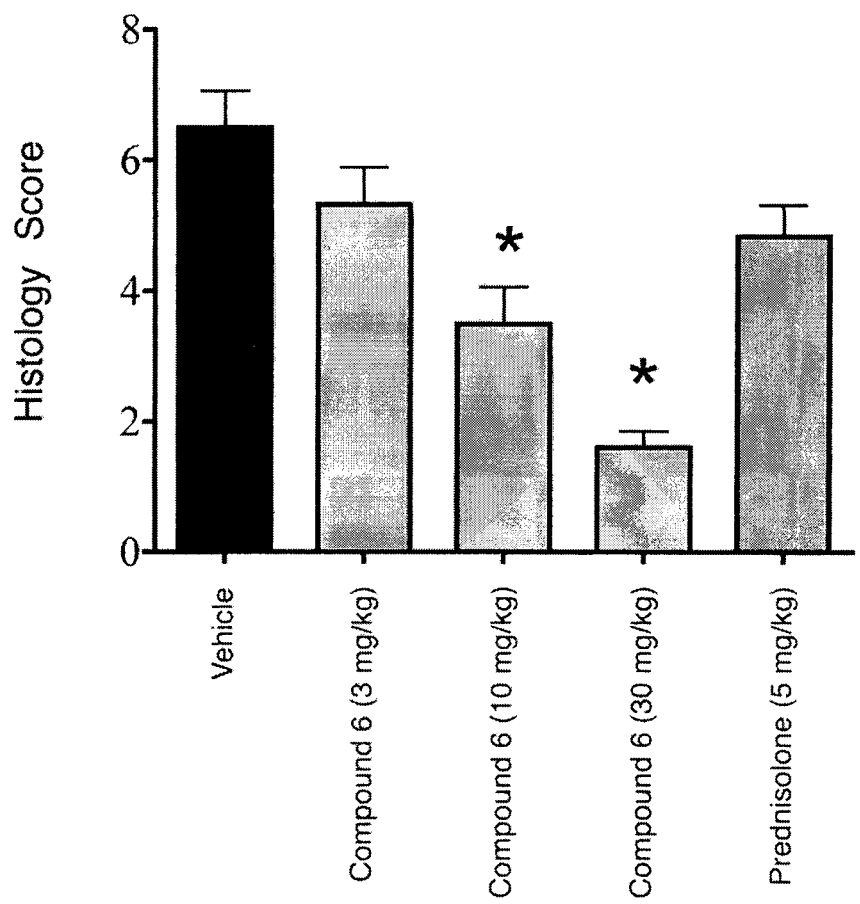
FIG. 12 Is a bar chart showing the effect of compound 6 on histology scores of colons from DSS-treated mice. Data are Mean±SEM from 5-6 mice. Asterisks indicate a significant (P<0.05) difference (1 way ANOVA) from the vehicle control group. Note, maximum score 10.

The extent of colon damage was quantified using an arbitrary scoring system. Compound 6 at both 10 and 30 mg/Kg, caused a dose-dependent and highly statistically significant reduction (P<0.01; Kruksal-Wallis ANOVA; Dunnett Multiple Comparison Test) in colon pathology relative to the vehicle group. In contrast, there was no significant improvement in histology scores with the prednisolone (5 mg/Kg) treated group relative to vehicle-treated mice (FIG. 12).

Figure 13:
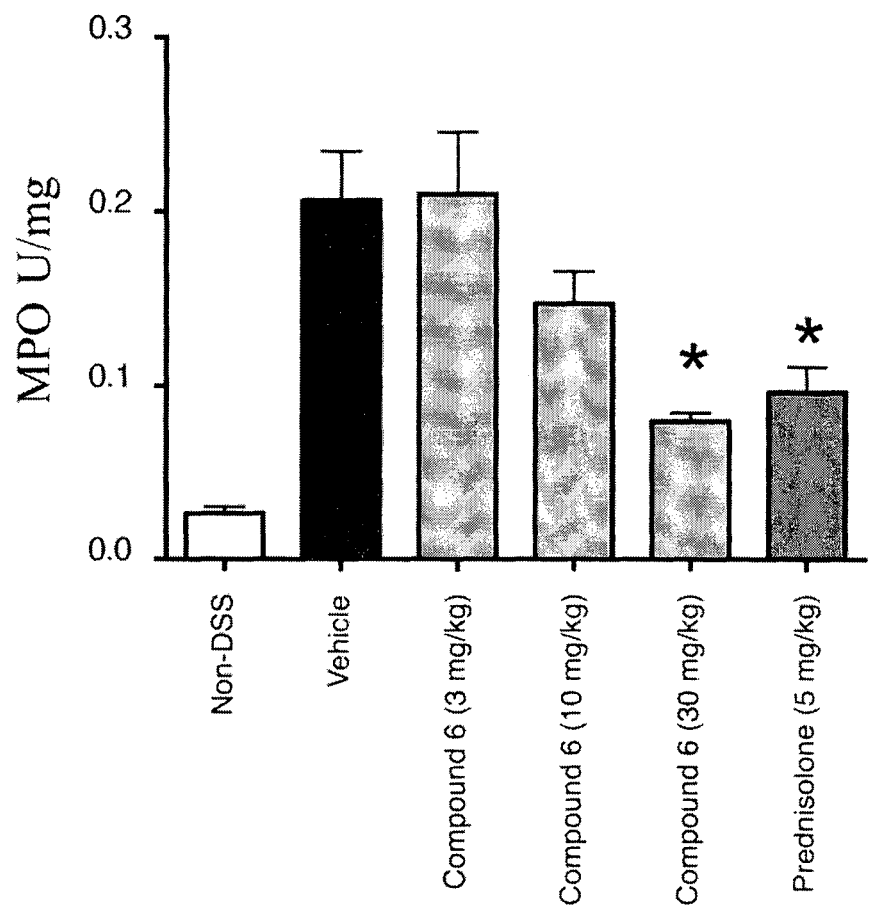
FIG. 13 Is a bar chart showing myeloperoxidase (MPO) activity in the colons of untreated or vehicle, prednisolone and compound 6 treated mice exposed to 5% DSS. Data are Mean±SEM from 5-6 mice. Asterisks indicate a significant (P<0.05) difference (1 way ANOVA) from the vehicle control group.

Consistent with the histology results showing inflammation in the colons of mice, there was a significant (P<0.001; Kruksal-Wallis ANOVA; Dunnett Multiple Comparison Test) elevation in colon myeloperoxidase (MPO) activity in DSS-treated mice administered vehicle only. Colonic myeloperoxidase activity (MPO), representing the level of inflammatory neutrophil cell infiltration into the gut wall which was increased by almost 8-fold by DSS treatment but was significantly (P<0.05) reduced by both compound 6 at 30 mg/kg and Prednisolone, at 63% and 54% respectively by day 7 (FIG. 13).

Figure 14A:
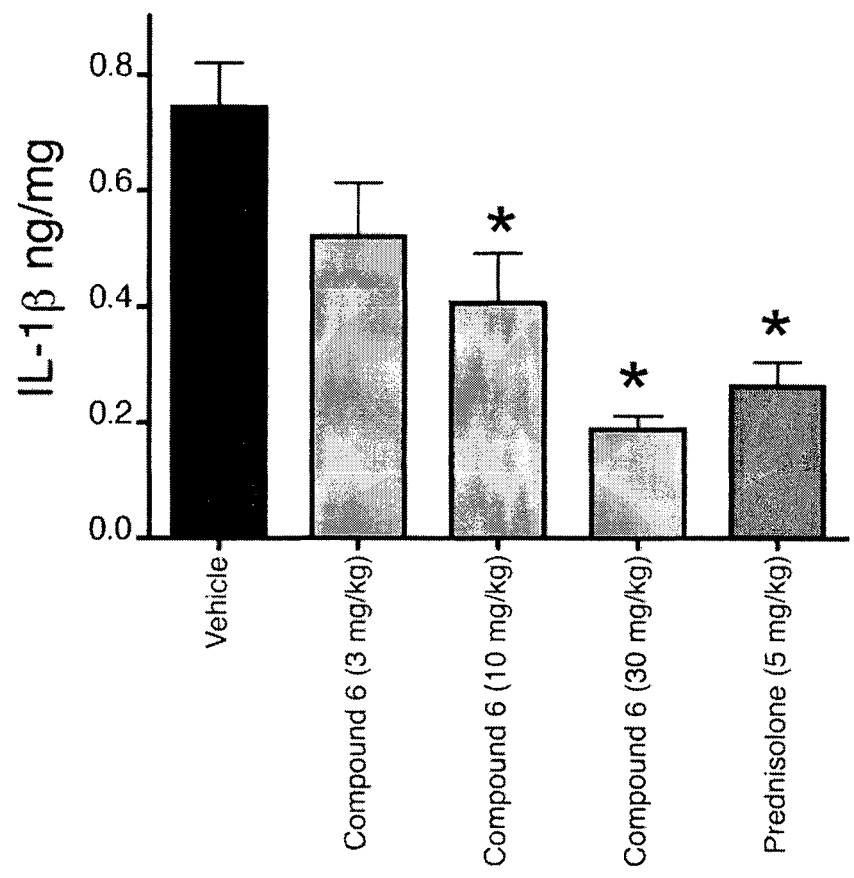
FIG. 14(A) to (C) are bar charts showing the effect of compound 6 on levels of cytokines (IL1β, TNFα and IL6) in mice treated with DSS. Data are Mean±SEM from 5-6 mice. Asterisks indicate a significant (P<0.05) difference (1 way ANOVA) from the vehicle control group.
Figure 14B:
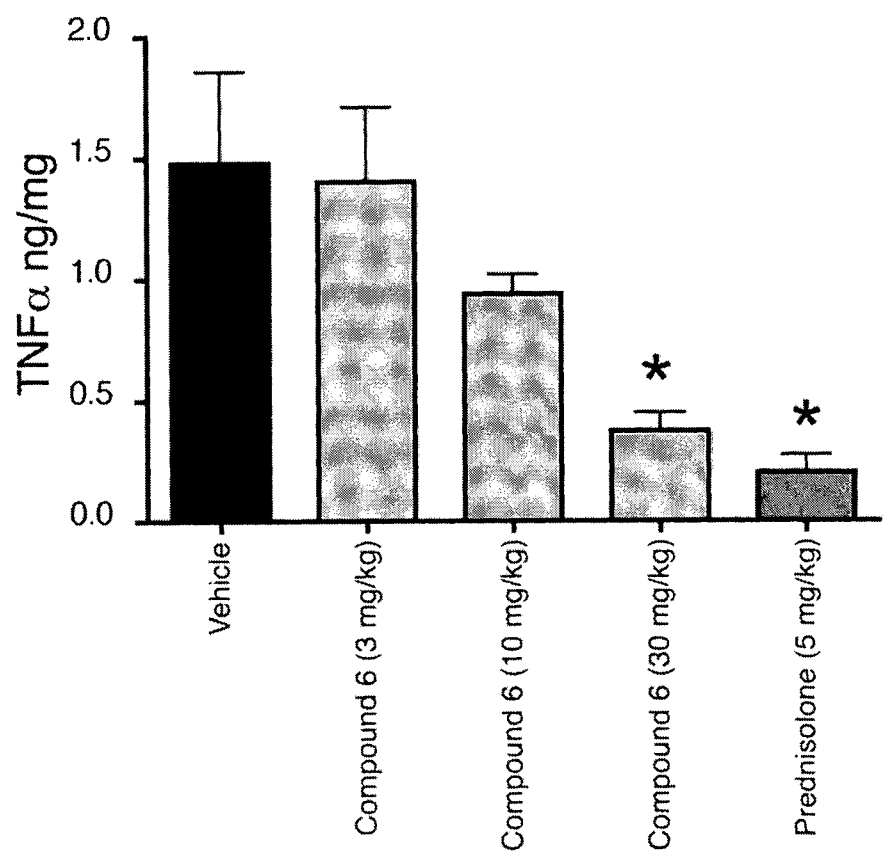
Figure 14C:
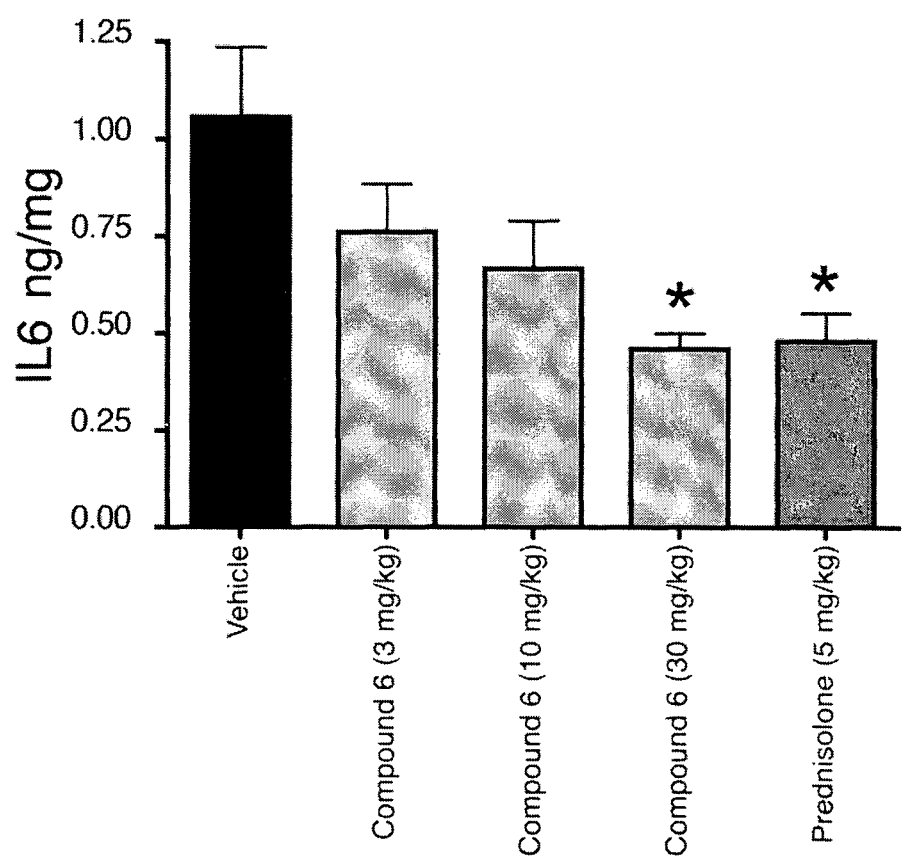

Quantification of levels of colon cytokines showed that DSS-treatment induces elevated IL1β (FIG. 14(a)), TNFα (FIG. 14(b)) and IL6 (FIG. 14(c)), to 0.744±0.076 ng/mg, 1.478±0.378 ng/mg and 1.057±0.1784 ng/mg respectively. In each case, compound 6 caused a significant (P<0.05, 30 mg/kg) and dose-dependant reduction in these cytokine levels. Prednisolone (5 mg/kg) also reduced (p<0.05) these increases in cytokine levels; for each cytokine there was no significant difference between the effect of prednisolone 5 mg/kg and compound 6 at the higher dose level of 30 mg/kg at day 7

In summary, following oral administration daily for 7 days, compound 6 at three doses (3, 10 and 30 mg/Kg) caused no overt reactions in mice. Compound 6 ameliorated the severity of colitis following acute 5% DSS treatment by multiple parameters of disease examined and the capacity to ameliorate the disease is dose-dependent. Further, compound 6 at 30 mg/Kg was therapeutic in the DSS model at a comparable or better efficacy, relative to prednisolone (5 mg/Kg).

Chronic $IL10^{-/-}$ Model

Figure 15:
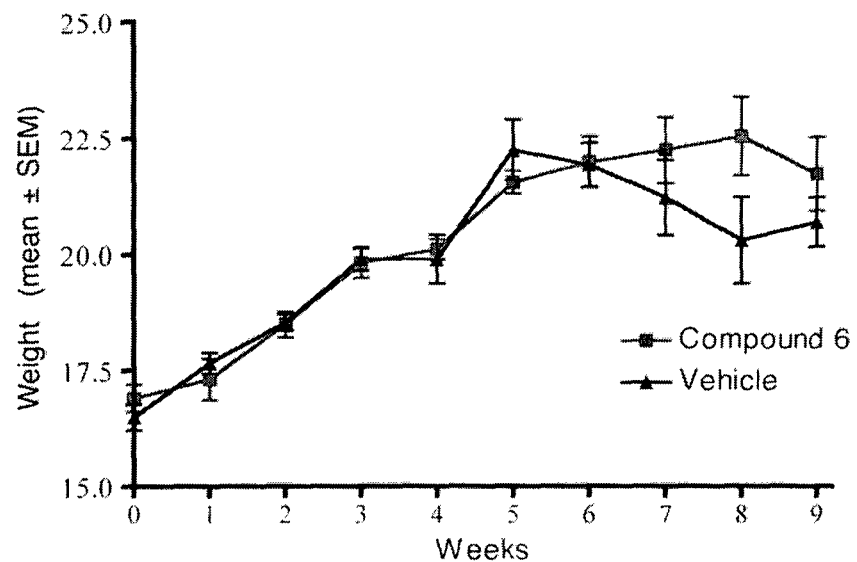
FIG. 15 Is a grph showing weight loss in IL10$^{-/-}$ mice treated with vehicle or compound 6. Mice were administered compound 6 (300 mg/kg/week) or vehicle orally on a Monday/Wednesday/Friday (MWF) dosing schedule. Mice were ~4 weeks of age at start of experiment and were treated for 9 weeks. Mice were weighed weekly and data are presented as Mean±SEM from 9-12 mice per group. Mice were monitored for overt disease, rectal prolapse, and moribund animals were humanely killed.
Figure 16:
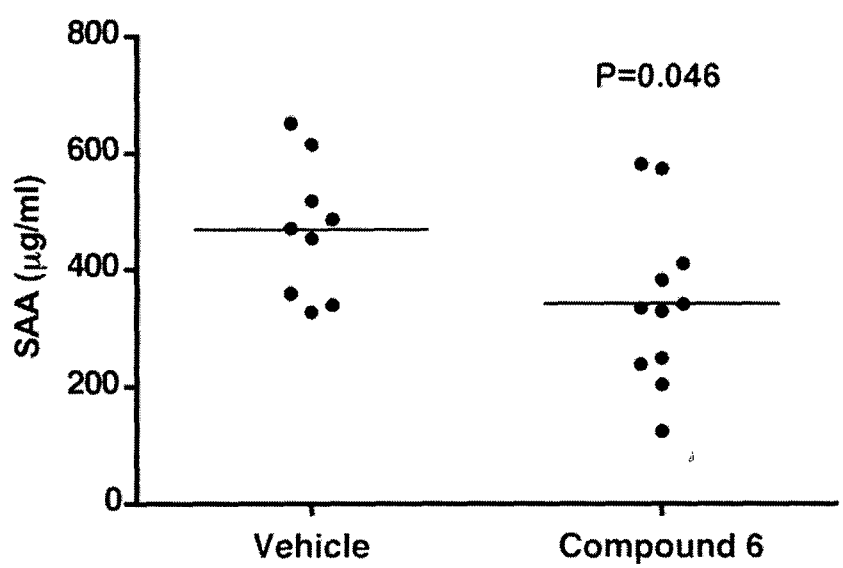
FIG. 16 Is a scatter graph representing Serum Amyloid A (SAA) levels of individual mice, and Mean (bar), from surviving animals at week 9 (11 and 9 mice in compound 6 or vehicle-treated groups, respectively). Student's t-test was used to test for statistical differences between groups.

Mice with a deletion in the $IL10^{-/-}$ gene spontaneously develop chronic colitis, with the age of onset and the severity of the disease being dependent on background mouse strain and the conditions in which the animals are housed. The onset of colitis in $IL10^{-/-}$ mice housed under the conditions used in this study was also strain dependent, with an earlier onset and greater severity, in terms of mortality, in BALB/c strain mice relative to C57BL/6 strain animals. In this experiment, animals received oral treatment on a MWF regime over 9 weeks. Initially, both groups of mice progressively gain weight (FIG. 15). Vehicle treated mice stopped gaining weight from week 5 of treatment, whereas compound 6-treated mice maintained weight gain until week 8. By week 9 animals had marked weight loss, with one moribund animal humanely killed on day 60 in each group. As other mice were losing weight and developing clinical symptoms of disease, both groups were culled at week 9 (day 63) and analysed. While there were greater mortalities in the vehicle-treated group (25%) relative to compound 6 treated mice (9.2%) by Kaplan-Meier analysis, there was no statistical difference in survival of IL10$^{-/-}$ mice over the 9 weeks. Serum was recovered from mice and Serum Amyloid A (SAA) and was analysed as a marker for severity of colitis. There were significantly (P<0.05; Student's t-test) reduced SAA levels in compound 6 treated mice relative to vehicle treated IL10$^{-/-}$ mice (FIG. 16).

Figure 17:
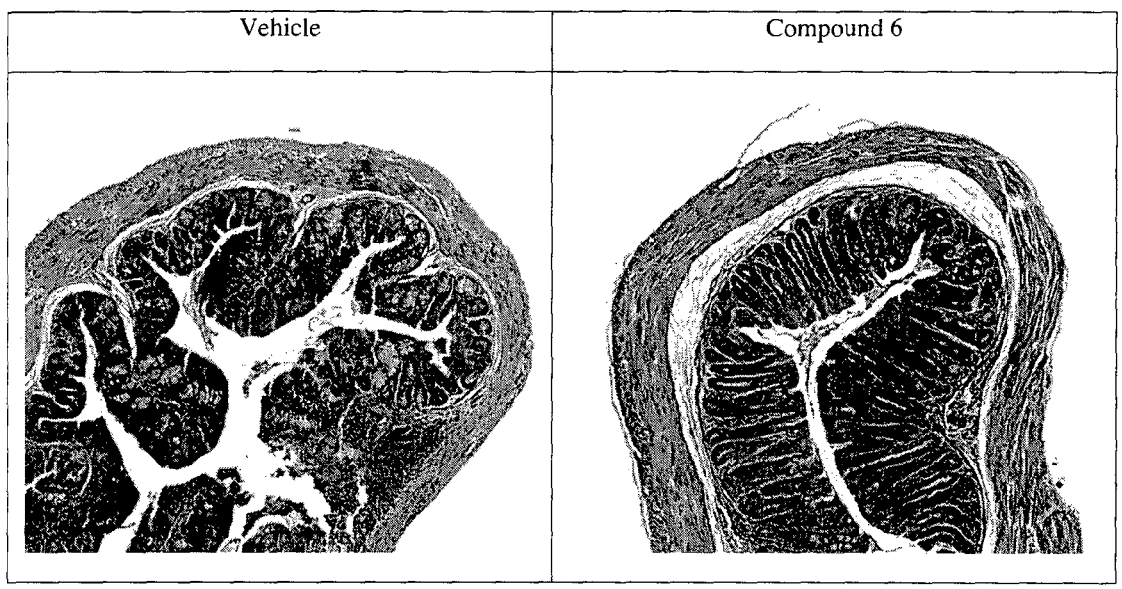
FIG. 17 Are representative hematoxylin and eosin-stained sections from distal colons from IL10$^{-/-}$ mice treated for 9 weeks with vehicle or compound 6.

Histology sections of colons from IL10$^{-/-}$ mice treated with vehicle or compound 6 are shown in FIG. 17.

Figure 18:
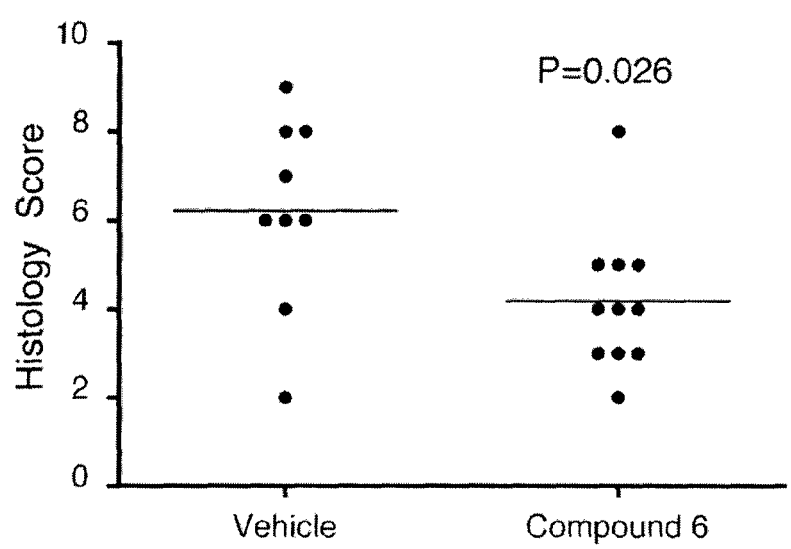
FIG. 18 Is a scatter graph showing histology scores of distal colons of IL10$^{-/-}$ mice treated with vehicle or compound 6. Scatter graph representing histology score of individual mice, and Mean (bar), from surviving animals at week 9 (11 and 9 mice in compound 6 or vehicle-treated groups, respectively). Student's t-test was used to test for statistical differences between groups.

Histology sections of colons from IL10$^{-/-}$ mice treated with vehicle or compound 6 were scored. The extent of colon pathology was significantly reduced (P<0.05; Student's t-test) in IL10$^{-/-}$ mice receiving compound relative to mice treated with vehicle (FIG. 18).

In summary, oral treatment with compound 6 (300 mg/kg/week) in IL10$^{-/-}$ BALB/c strain mice, using a MWF regime over 9 weeks, delayed weight loss and reduced deaths from colitis relative to vehicle-treated mice. In this model of chronic colitis, compound 6 significantly reduced disease indices with respect to a serum marker of colon inflammation and the degree of inflammation and damage to the colon. This is particularly noteworthy in view of the fact that the plasma half-life ($t_{1/2}$) for compound 6 is 3 hours in the rat. With the standard MWF dosing schedule, mice will have been unexposed to compound 6 for substantial periods during the experiment.

The invention is not limited to the embodiments hereinbefore described which may be varied in detail.

APPENDIX 1

List of Abbreviations Used aq aqueous
b.p. boiling point
CDCl$_3$ chloroform-d
CH(OCH$_3$)$_3$ trimethylsilyl orthoformate
CO$_2$ carbon dioxide
DCM dichloromethane
dIW distilled ionized water
DMSO dimethyl sulphoxide
Et$_2$O ether
EtOH ethanol
H$_2$O water
HCl hydrochloric acid
IR infra red
IPA isopropyl alcohol
KCl potassium chloride
M molar
min minutes
microliters
mM milli-molar
m.p. melting point
N$_2$ nitrogen
NaBH$_4$ sodium borohydride
NaOH sodium hydroxide
Na$_2$SO$_4$ sodium sulphate
NMR nuclear magnetic resonance
O$_2$ oxygen
RT room temperature
$^t$BuOH tert butanol
$^t$BuOK potassium tert butoxide
S.E.M. standard error of mean
THF tetrahydrofuran
TLC thin layer chromatography
μl microliters Triflic Acid trifluoromethanesulfonic acid
TMS Triflate trimethyl silyl trifluoromethanesulfonate
v/v volume per volume
w/v weight per volume
$\lambda_{em}$ emission wavelength
$\lambda_{exc}$ excitation wavelength

APPENDIX 2

X-Ray Studies

A single crystal X-ray analysis was carried out on compound 2 (S)-(–)-methylbenzylamine salt (compound 8), using a SuperNova, Dual, Cu at zero, Atlas Diffractometer and the parameters outlined in Table 1.

TABLE 1

Data collection and structure refinement for compound 8, the (S)-(–)-methylbenzylamine salt of compound 2.

| | |
|---|---|
| Diffractometer | SuperNova, Dual, Cu at zero, Atlas |
| Radiation source | SuperNova (Cu) X-ray Source, Cu Kα |
| Data collection method | Omega scans |
| Theta range for data collection | 3.74 to 76.22° |
| Index ranges | $-13 \leq h \leq 13$, $-11 \leq k \leq 12$, $-14 \leq l \leq 14$ |
| Reflections collected | 12753 |
| Independent reflections | 5263 [R(int) = 0.0196] |
| Coverage of independent reflections | 99.4% |
| Variation in check reflections | N/A |
| Absorption correction | Semi-empirical from equivalents |
| Max. and min. transmission | 1.00000 and 0.90238 |
| Structure solution technique | direct |
| Structure solution program | Bruker SHELXTL |
| Refinement technique | Full-matrix least-squares on $F^2$ |
| Refinement program | Bruker SHELXTL |
| Function minimized | $\Sigma w(F_o^2 - F_c^2)^2$ |
| Data/restraints/parameters | 5263/1/363 |
| Goodness-of-fit on $F^2$ | 1.007 |
| $\Delta/\sigma_{max}$ | 0.001 |
| Final R indices | |
| 5161 data; I > 2σ(I) | R1 = 0.0321, wR2 = 0.0857 |
| all data | R1 = 0.0327, wR2 = 0.0865 |
| Weighting scheme | $w = 1/[\sigma^2 (F_o^2) + (0.0600P)^2 + 0.2200P]$ where $P = (F_o^2 + 2F_c^2)/3$ |
| Absolute structure parameter | 0.04(14) |
| Extinction coefficient | 0.0035(5) |
| Largest diff. peak and hole | 0.214 and −0.154 e Å$^{-3}$ |

Refinement Summary:

Ordered Non-H atoms, XYZ Freely refining

Ordered Non-H atoms, U Anisotropic

H atoms (on carbon), XYZ Idealized positions riding on attached atoms

H atoms (on carbon), U Appropriate multiple of U(eq) for bonded atom

H atoms (on heteroatoms), XYZ Freely refining

H atoms (on heteroatoms), U Isotropic

Disordered atoms, OCC Refined with a two part model constrained to a total of unity Disordered atoms, XYZ freely refining Disordered atoms, U freely refining The single crystal X-ray data establishes that the structure of compound 6 is monoclinic, space group P2$_1$, with one molecule of compound 6 in the asymmetric unit (Table 2).

TABLE 2

Sample and crystal data for compound 8

| | |
|---|---|
| Crystallization solvents | Diethyl ether, MeOH, THF |
| Crystallization method | Slow evaporation |
| Empirical formula | $C_{34}H_{33}N_1O_3$ |
| Formula weight | 503.61 |
| Temperature | 100(1) K |
| Wavelength | 1.54178 Å |
| Crystal size | 0.50 × 0.50 × 0.50 mm |
| Crystal habit | Colourless Block |
| Crystal system | Monoclinic |
| Space group | $P2_1$ |
| Unit cell dimensions | a = 11.0344(2) Å  α = 90° |
| | b = 10.1727(2) Å  β = 93.682(2)° |
| | c = 11.8532(2) Å  γ = 90° |
| Volume | 1327.77(4) Å³ |
| Z | 2 |
| Density (calculated) | 1.260 Mg/m³ |
| Absorption coefficient | 0.627 mm⁻¹ |
| F(000) | 536 |

The absolute stereochemistry was determined as S, S at C9 and C10 for compound 2 and S at C33 for the methylbenzylamine cation. The assignment was made from consideration of both the Flack parameter which was determined to be 0.04 (14) and from the a priori knowledge of the stereochemistry of the salt former.

The absolute stereochemistry was also determined using Bayesian statistics on the Bijvoet pair differences which resulted in a probability of the stereochemistry at the chiral centers C9, C10 and C33 being S, S and S respectively as 1.000 and R, R and R as 0.000. This supports the assignment of S, S and S for C9, C10 and C33 respectively from the Flack parameter measurement.

The calculated X-ray powder diffraction pattern from the single crystal X-ray structure was in agreement with the stereochemistry shown in FIG. 2 (or the following).

TABLE 3

Atomic coordinates and equivalent isotropic, atomic displacement parameters, (Å²), for compound 8. U(eq) is defined as one third of the trace of the orthogonalised $U_{ij}$ tensor.

| | x/a | y/b | z/c | U(eq) |
|---|---|---|---|---|
| O1 | 0.02763(10) | 0.17316(11) | 1.16556(8) | 0.0228(2) |
| O2 | 0.07430(9) | −0.03465(10) | 1.12294(7) | 0.0194(2) |
| O3 | 0.10561(8) | 0.01057(10) | 1.90142(8) | 0.0184(2) |
| C1 | 0.08315(12) | −0.12167(14) | 1.47373(12) | 0.0198(3) |
| C2 | 0.07248(13) | −0.09752(14) | 1.35802(12) | 0.0192(3) |
| C3 | 0.08014(11) | 0.02912(13) | 1.31666(11) | 0.0158(3) |
| C4 | 0.05975(11) | 0.05851(14) | 1.19195(11) | 0.0164(3) |
| C5 | 0.10196(12) | 0.13219(14) | 1.39262(11) | 0.0184(3) |
| C6 | 0.11261(13) | 0.10790(14) | 1.50817(11) | 0.0197(3) |
| C7 | 0.10101(11) | −0.01884(14) | 1.55106(10) | 0.0164(3) |
| C8 | 0.09988(12) | −0.04205(14) | 1.67717(10) | 0.0177(3) |
| C9 | 0.22568(11) | −0.05199(14) | 1.74191(10) | 0.0160(3) |
| C10 | 0.20981(12) | −0.06390(14) | 1.87231(10) | 0.0173(3) |
| C11 | 0.32285(12) | −0.00001(14) | 1.92450(11) | 0.0183(3) |
| C12 | 0.36695(13) | −0.00323(15) | 2.03747(11) | 0.0217(3) |
| C13 | 0.46523(13) | 0.07703(16) | 2.07067(12) | 0.0263(3) |
| C14 | 0.51796(13) | 0.15733(16) | 1.99312(13) | 0.0271(3) |
| C15 | 0.47368(13) | 0.16061(15) | 1.87974(13) | 0.0237(3) |
| C16 | 0.37476(12) | 0.08173(14) | 1.84684(11) | 0.0188(3) |
| C17 | 0.30303(12) | 0.07486(14) | 1.73362(11) | 0.0189(3) |
| C18 | 0.29536(12) | −0.17122(14) | 1.70380(10) | 0.0170(3) |
| C19 | 0.24493(13) | −0.29849(15) | 1.68674(11) | 0.0224(3) |
| C20 | 0.34284(13) | −0.38466(15) | 1.64945(10) | 0.0202(3) |
| C21 | 0.34340(15) | −0.51740(16) | 1.62093(12) | 0.0279(3) |
| C22 | 0.45250(18) | −0.57426(17) | 1.59308(13) | 0.0363(8) |
| C23 | 0.55837(16) | −0.50075(18) | 1.59165(13) | 0.0317(4) |
| C24 | 0.55735(14) | −0.36697(17) | 1.61785(12) | 0.0269(3) |
| C25 | 0.44911(13) | −0.31016(15) | 1.64729(11) | 0.0212(3) |

TABLE 3-continued

Atomic coordinates and equivalent isotropic, atomic displacement parameters, (Å²), for compound 8. U(eq) is defined as one third of the trace of the orthogonalised $U_{ij}$ tensor.

| | x/a | y/b | z/c | U(eq) |
|---|---|---|---|---|
| C26 | 0.42215(14) | −0.17370(16) | 1.68241(12) | 0.0238(3) |
| C18A | 0.29536(12) | −0.17122(14) | 1.70380(10) | 0.0170(3) |
| C19A | 0.24493(13) | −0.29849(15) | 1.68674(11) | 0.0224(3) |
| C20A | 0.34284(13) | −0.38466(15) | 1.64945(10) | 0.0202(3) |
| C21A | 0.34340(15) | −0.51740(16) | 1.62093(12) | 0.0279(3) |
| C22A | 0.45250(18) | −0.57426(17) | 1.59308(13) | 0.0279(3) |
| C23A | 0.55837(16) | −0.50075(18) | 1.59165(13) | 0.0317(4) |
| C24A | 0.55735(14) | −0.36697(17) | 1.61785(12) | 0.0269(3) |
| C25A | 0.44911(13) | −0.31016(15) | 1.64729(11) | 0.0212(3) |
| C26A | 0.42215(14) | −0.17370(16) | 1.68241(12) | 0.0238(3) |
| N1 | −0.09024(11) | −0.21952(13) | 1.02800(10) | 0.0194(2) |
| C27 | −0.18541(12) | 0.06679(15) | 0.92258(12) | 0.0220(3) |
| C28 | −0.19466(13) | 0.15069(16) | 0.82981(13) | 0.0256(3) |
| C29 | −0.23606(14) | 0.10317(17) | 0.72421(13) | 0.0273(3) |
| C30 | −0.26855(15) | −0.02757(18) | 0.71195(13) | 0.0301(3) |
| C31 | −0.26063(14) | −0.11089(16) | 0.80481(13) | 0.0255(3) |
| C32 | −0.21928(12) | −0.06417(15) | 0.91135(11) | 0.0200(3) |
| C33 | −0.21444(12) | −0.15827(15) | 1.01084(12) | 0.0205(3) |
| C34 | −0.24587(14) | −0.09613(16) | 1.12172(13) | 0.0256(3) |

TABLE 4

Selected bond lengths, (Å), for compound 8

| O1—C4 | 1.2528(18) | O2—C4 | 1.2688(17) |
|---|---|---|---|
| O3—C10 | 1.4373(16) | O3—H3A | 0.88(2) |
| C1—C2 | 1.3909(19) | C1—C7 | 1.3964(19) |
| C2—C3 | 1.383(2) | C3—C5 | 1.3929(19) |
| C3—C4 | 1.5108(17) | C5—C6 | 1.3893(18) |
| C6—C7 | 1.395(2) | C7—C8 | 1.5141(16) |
| C8—C9 | 1.5457(17) | C9—C18 | 1.5203(19) |
| C9—C17 | 1.5537(19) | C9—C10 | 1.5713(16) |
| C10—C11 | 1.5040(18) | C11—C16 | 1.391(2) |
| C11—C12 | 1.3953(17) | C12—C13 | 1.394(2) |
| C13—C14 | 1.385(2) | C14—C15 | 1.401(2) |
| C15—C16 | 1.390(2) | C16—C17 | 1.5152(18) |
| C18—C19 | 1.418(2) | C18—C26 | 1.4380(19) |
| C19—C20 | 1.481(2) | C20—C21 | 1.392(2) |
| C20—C25 | 1.398(2) | C21—C22 | 1.394(2) |
| C22—C23 | 1.388(3) | C23—C24 | 1.396(2) |
| C24—C25 | 1.391(2) | C25—C26 | 1.485(2) |
| N1—C33 | 1.5073(18) | N1—H1B | 0.91(2) |
| N1—H1C | 0.93(2) | N1—H1D | 0.90(2) |
| C27—C32 | 1.388(2) | C27—C28 | 1.390(2) |
| C28—C29 | 1.391(2) | C29—C30 | 1.383(3) |
| C30—C31 | 1.387(2) | C31—C32 | 1.398(2) |
| C32—C33 | 1.5172(19) | C33—C34 | 1.518(2) |

TABLE 5

Selected bond angles, (°), for compound 8

| C10—O3—H3A | 107.0(15) | C2—C1—C7 | 120.96(13) |
|---|---|---|---|
| C3—C2—C1 | 120.72(13) | C2—C3—C5 | 118.95(12) |
| C2—C3—C4 | 121.50(12) | C5—C3—C4 | 119.48(12) |
| O1—C4—O2 | 125.44(12) | O1—C4—C3 | 116.78(12) |
| O2—C4—C3 | 117.77(12) | C6—C5—C3 | 120.23(13) |
| C5—C6—C7 | 121.32(13) | C6—C7—C1 | 117.75(12) |
| C6—C7—C8 | 120.71(12) | C1—C7—C8 | 121.43(13) |
| C7—C8—C9 | 115.87(10) | C18—C9—C8 | 111.09(11) |
| C18—C9—C17 | 110.70(11) | C8—C9—C17 | 113.19(11) |
| C18—C9—C10 | 108.74(10) | C8—C9—C10 | 109.89(10) |
| C17—C9—C10 | 102.86(10) | O3—C10—C11 | 109.18(11) |
| O3—C10—C9 | 109.69(10) | C11—C10—C9 | 103.26(10) |
| C16—C11—C12 | 121.07(13) | C16—C11—C10 | 110.61(11) |
| C12—C11—C10 | 127.84(13) | C13—C12—C11 | 118.29(14) |
| C14—C13—C12 | 120.72(13) | C13—C14—C15 | 120.99(14) |
| C16—C15—C14 | 118.34(14) | C15—C16—C11 | 120.58(13) |
| C15—C16—C17 | 129.14(13) | C11—C16—C17 | 110.16(12) |

TABLE 5-continued

Selected bond angles, (°), for compound 8

| | | | | | | | |
|---|---|---|---|---|---|---|---|
| C16—C17—C9 | 103.90(11) | C19—C18—C26 | 109.64(13) | H1B—N1—H1C | 107.4(18) | C33—N1—H1D | 111.6(13) |
| C19—C18—C9 | 124.70(12) | C26—C18—C9 | 125.65(13) | H1B—N1—H1D | 112.5(18) | H1C—N1—H1D | 105.0(17) |
| C18—C19—C20 | 107.21(12) | C21—C20—C25 | 120.31(14) | C32—C27—C28 | 120.51(14) | C27—C28—C29 | 120.09(15) |
| C21—C20—C19 | 131.41(14) | C25—C20—C19 | 108.27(13) | C30—C29—C28 | 119.78(14) | C29—C30—C31 | 120.10(14) |
| C20—C21—C22 | 118.51(15) | C23—C22—C21 | 121.31(15) | C30—C31—C32 | 120.61(15) | C27—C32—C31 | 118.89(14) |
| C22—C23—C24 | 120.24(15) | C25—C24—C23 | 118.68(15) | C27—C32—C33 | 122.36(13) | C31—C32—C33 | 118.74(13) |
| C24—C25—C20 | 120.94(14) | C24—C25—C26 | 130.48(14) | N1—C33—C32 | 110.61(11) | N1—C33—C34 | 108.16(11) |
| C20—C25—C26 | 108.57(13) | C18—C26—C25 | 106.29(13) | C32—C33—C34 | 114.30(12) | | |
| C33—N1—H1B | 108.3(13) | C33—N1—H1C | 112.0(13) | | | | |

TABLE 6

Selected torsion angles, (°), for compound 8

| | | | |
|---|---|---|---|
| C7—C1—C2—C3 | 0.4(2) | C1—C2—C3—C5 | 1.7(2) |
| C1—C2—C3—C4 | −175.50(12) | C2—C3—C4—O1 | 156.41(13) |
| C5—C3—C4—O1 | −20.75(18) | C2—C3—C4—O2 | −22.38(18) |
| C5—C3—C4—O2 | 160.46(12) | C2—C3—C5—C6 | −1.7(2) |
| C4—C3—C5—C6 | 175.57(12) | C3—C5—C6—C7 | −0.5(2) |
| C5—C6—C7—C1 | 2.5(2) | C5—C6—C7—C8 | −173.65(12) |
| C2—C1—C7—C6 | −2.52(19) | C2—C1—C7—C8 | 173.64(12) |
| C6—C7—C8—C9 | −83.92(16) | C1—C7—C8—C9 | 100.03(15) |
| C7—C8—C9—C18 | −64.43(16) | C7—C8—C9—C17 | 60.83(15) |
| C7—C8—C9—C10 | 175.19(12) | C18—C9—C10—O3 | −155.49(11) |
| C8—C9—C10—O3 | −33.70(15) | C17—C9—C10—O3 | 87.10(12) |
| C18—C9—C10—C11 | 88.22(13) | C8—C9—C10—C11 | −149.99(11) |
| C17—C9—C10—C11 | −29.19(13) | O3—C10—C11—C16 | −96.36(13) |
| C9—C10—C11—C16 | 20.29(15) | O3—C10—C11—C12 | 75.67(18) |
| C9—C10—C11—C12 | −167.68(14) | C16—C11—C12—C13 | −0.5(2) |
| C10—C11—C12—C13 | −171.75(13) | C11—C12—C13—C14 | −0.3(2) |
| C12—C13—C14—C15 | 0.3(2) | C13—C14—C15—C16 | 0.4(2) |
| C14—C15—C16—C11 | −1.2(2) | C14—C15—C16—C17 | 174.32(14) |
| C12—C11—C16—C15 | 1.2(2) | C10—C11—C16—C15 | 173.88(13) |
| C12—C11—C16—C17 | −175.05(12) | C10—C11—C16—C17 | −2.40(16) |
| C15—C16—C17—C9 | 167.34(14) | C11—C16—C17—C9 | −16.79(15) |
| C18—C9—C17—C16 | −88.09(12) | C8—C9—C17—C16 | 146.44(11) |
| C10—C9—C17—C16 | 27.92(13) | C8—C9—C18—C19 | −44.46(16) |
| C17—C9—C18—C19 | −171.10(11) | C10—C9—C18—C19 | 76.60(15) |
| C8—C9—C18—C26 | 137.25(13) | C17—C9—C18—C26 | 10.60(17) |
| C10—C9—C18—C26 | −101.70(15) | C26—C18—C19—C20 | −1.81(14) |
| C9—C18—C19—C20 | 179.67(11) | C18—C19—C20—C21 | −179.77(14) |
| C18—C19—C20—C25 | 1.34(15) | C25—C20—C21—C22 | 1.5(2) |
| C19—C20—C21—C22 | −177.24(14) | C20—C21—C22—C23 | −1.1(2) |
| C21—C22—C23—C24 | −0.3(2) | C22—C23—C24—C25 | 1.2(2) |
| C23—C24—C25—C20 | −0.7(2) | C23—C24—C25—C26 | 177.73(14) |
| C21—C20—C25—C24 | −0.6(2) | C19—C20—C25—C24 | 178.39(12) |
| C21—C20—C25—C26 | −179.41(12) | C19—C20—C25—C26 | −0.38(15) |
| C19—C18—C26—C25 | 1.57(15) | C9—C18—C26—C25 | −179.92(11) |
| C24—C25—C26—C18 | −179.32(14) | C20—C25—C26—C18 | −0.71(15) |
| C32—C27—C28—C29 | −1.2(2) | C27—C28—C29—C30 | 0.3(2) |
| C28—C29—C30—C31 | 0.4(2) | C29—C30—C31—C32 | −0.3(2) |
| C28—C27—C32—C31 | 1.2(2) | C28—C27—C32—C33 | −178.07(13) |
| C30—C31—C32—C27 | −0.5(2) | C30—C31—C32—C33 | 178.85(14) |
| C27—C32—C33—N1 | −86.99(16) | C31—C32—C33—N1 | 93.72(15) |
| C27—C32—C33—C34 | 35.36(18) | C31—C32—C33—C34 | −143.93(14) |

TABLE 7

Anisotropic atomic displacement parameters, (Å$^2$), for compound 8 The anistropic atomic displacement factor exponent takes the form: $-2\pi^2$ [h$^2$a*$^2$ U$_{11}$ + ... + 2hka* b* U$_{12}$

| | U$_{11}$ | U$_{22}$ | U$_{33}$ | U$_{23}$ | U$_{13}$ | U$_{12}$ |
|---|---|---|---|---|---|---|
| O1 | 0.0325(5) | 0.0206(5) | 0.0153(4) | 0.0025(4) | 0.0015(4) | 0.0044(4) |
| O2 | 0.0255(5) | 0.0206(5) | 0.0123(4) | −0.0017(4) | 0.0024(3) | −0.0014(4) |
| O3 | 0.0205(4) | 0.0232(5) | 0.0116(4) | −0.0002(4) | 0.0027(3) | 0.0016(4) |
| C1 | 0.0257(7) | 0.0179(7) | 0.0159(6) | 0.0017(5) | 0.0018(5) | −0.0028(5) |
| C2 | 0.0267(7) | 0.0171(7) | 0.0139(6) | −0.0035(5) | 0.0024(5) | −0.0019(5) |
| C3 | 0.0160(6) | 0.0187(7) | 0.0128(6) | −0.0004(5) | 0.0017(4) | 0.0011(5) |
| C4 | 0.0166(5) | 0.0193(7) | 0.0134(6) | 0.0000(4) | 0.0014(4) | −0.0018(5) |
| C5 | 0.0234(6) | 0.0155(7) | 0.0159(6) | −0.0001(5) | −0.0011(5) | 0.0020(5) |
| C6 | 0.0251(6) | 0.0175(7) | 0.0158(6) | −0.0030(5) | −0.0024(5) | 0.0028(5) |
| C7 | 0.0150(5) | 0.0213(7) | 0.0129(6) | 0.0000(5) | 0.0009(4) | 0.0028(5) |
| C8 | 0.0188(6) | 0.0217(7) | 0.0124(6) | −0.0007(5) | 0.0000(4) | 0.0018(5) |

TABLE 7-continued

Anisotropic atomic displacement parameters, (Å$^2$), for compound 8 The anistropic atomic displacement factor exponent takes the form: $-2\pi^2 [h^2a^{*2} U_{11} + \ldots + 2hka^* b^* U_{12}]$

|      | $U_{11}$   | $U_{22}$   | $U_{33}$   | $U_{23}$    | $U_{13}$    | $U_{12}$     |
|------|------------|------------|------------|-------------|-------------|--------------|
| C9   | 0.0186(6)  | 0.0177(7)  | 0.0117(5)  | 0.0004(5)   | 0.0007(4)   | −0.0002(5)   |
| C10  | 0.0206(6)  | 0.0190(7)  | 0.0121(6)  | 0.0000(5)   | 0.0005(4)   | 0.0022(5)    |
| C11  | 0.0201(6)  | 0.0185(7)  | 0.0163(6)  | −0.0030(5)  | 0.0004(5)   | 0.0033(5)    |
| C12  | 0.0234(6)  | 0.0249(8)  | 0.0166(6)  | −0.0018(5)  | −0.0015(5)  | 0.0056(5)    |
| C13  | 0.0237(7)  | 0.0322(9)  | 0.0216(7)  | −0.0074(6)  | −0.0074(5)  | 0.0074(6)    |
| C14  | 0.0196(7)  | 0.0284(8)  | 0.0324(8)  | −0.0099(6)  | −0.0049(6)  | 0.0015(6)    |
| C15  | 0.0199(6)  | 0.0229(7)  | 0.0282(7)  | −0.0035(6)  | 0.0008(5)   | 0.0012(6)    |
| C16  | 0.0186(6)  | 0.0198(7)  | 0.0178(6)  | −0.0023(5)  | 0.0007(5)   | 0.0028(5)    |
| C17  | 0.0213(6)  | 0.0203(7)  | 0.0151(6)  | 0.0004(5)   | 0.0018(5)   | −0.0008(5)   |
| C18  | 0.0200(6)  | 0.0206(7)  | 0.0101(5)  | 0.0011(5)   | −0.0009(4)  | 0.0004(5)    |
| C19  | 0.0245(7)  | 0.0249(8)  | 0.0176(6)  | −0.0024(5)  | 0.0008(5)   | 0.0029(5)    |
| C20  | 0.0256(7)  | 0.0227(7)  | 0.0124(6)  | 0.0001(5)   | 0.0015(5)   | 0.0027(5)    |
| C21  | 0.0392(8)  | 0.0237(8)  | 0.0215(6)  | −0.0032(6)  | 0.0059(6)   | −0.0017(7)   |
| C22  | 0.063(2)   | 0.0236(16) | 0.0226(13) | −0.0024(11) | 0.0090(13)  | 0.0165(15)   |
| C23  | 0.0359(8)  | 0.0356(9)  | 0.0240(7)  | −0.0034(6)  | 0.0049(6)   | 0.0140(7)    |
| C24  | 0.0253(7)  | 0.0331(9)  | 0.0225(7)  | −0.0050(6)  | 0.0034(6)   | 0.0047(6)    |
| C25  | 0.0253(7)  | 0.0253(8)  | 0.0129(5)  | 0.0003(5)   | 0.0016(5)   | 0.0035(5)    |
| C26  | 0.0277(7)  | 0.0248(8)  | 0.0197(6)  | −0.0005(6)  | 0.0069(5)   | 0.0012(6)    |
| C18A | 0.0200(6)  | 0.0206(7)  | 0.0101(5)  | 0.0011(5)   | −0.0009(4)  | 0.0004(5)    |
| C19A | 0.0245(7)  | 0.0249(8)  | 0.0176(6)  | −0.0024(5)  | 0.0008(5)   | 0.0029(5)    |
| C20A | 0.0256(7)  | 0.0227(7)  | 0.0124(6)  | 0.0001(5)   | 0.0015(5)   | 0.0027(5)    |
| C21A | 0.0392(8)  | 0.0237(8)  | 0.0215(6)  | −0.0032(6)  | 0.0059(6)   | −0.0017(7)   |
| C22A | 0.0392(8)  | 0.0237(8)  | 0.0215(6)  | −0.0032(6)  | 0.0059(6)   | −0.0017(7)   |
| C23A | 0.0359(8)  | 0.0356(9)  | 0.0240(7)  | −0.0034(6)  | 0.0049(6)   | 0.0140(7)    |
| C24A | 0.0253(7)  | 0.0331(9)  | 0.0225(7)  | −0.0050(6)  | 0.0034(6)   | 0.0047(6)    |
| C25A | 0.0253(7)  | 0.0253(8)  | 0.0129(5)  | 0.0003(5)   | 0.0016(5)   | 0.0035(5)    |
| C26A | 0.0277(7)  | 0.0248(8)  | 0.0197(6)  | −0.0005(6)  | 0.0069(5)   | 0.0012(6)    |
| N1   | 0.0248(6)  | 0.0191(6)  | 0.0143(5)  | −0.0013(5)  | 0.0005(4)   | −0.0007(5)   |
| C27  | 0.0216(6)  | 0.0233(7)  | 0.0213(7)  | −0.0001(5)  | 0.0017(5)   | −0.0030(5)   |
| C28  | 0.0250(7)  | 0.0228(8)  | 0.0293(7)  | 0.0035(6)   | 0.0038(6)   | −0.0021(6)   |
| C29  | 0.0265(7)  | 0.0298(9)  | 0.0254(7)  | 0.0087(6)   | −0.0001(5)  | −0.0017(6)   |
| C30  | 0.0326(8)  | 0.0357(9)  | 0.0214(7)  | 0.0019(6)   | −0.0041(6)  | −0.0050(7)   |
| C31  | 0.0286(7)  | 0.0238(8)  | 0.0234(7)  | 0.0001(6)   | −0.0034(6)  | −0.0053(6)   |
| C32  | 0.0169(6)  | 0.0233(7)  | 0.0198(6)  | 0.0024(5)   | 0.0007(5)   | −0.0024(5)   |
| C33  | 0.0196(6)  | 0.0205(7)  | 0.0212(6)  | 0.0023(5)   | 0.0001(5)   | −0.0031(5)   |
| C34  | 0.0280(7)  | 0.0264(8)  | 0.0232(7)  | 0.0029(6)   | 0.0065(6)   | 0.0024(6)    |

APPENDIX 3

Compound 1 4-((−1-hydroxy-2,3-dihydro-1H,1'H-2,2'-biinden-2-yl)methyl)benzoic acid Compound 2 4-(((1S,2S)-1-hydroxy-2,3-dihydro-1H,1'H-2,2'-biinden-2-yl)methyl)benzoic acid Compound 3 4-(((1R,2R)-1-hydroxy-2,3-dihydro-1H,'1'H-2,2'-biinden-2-yl)methyl)benzoic acid Compound 4 4-(((1R,2S)-1-hydroxy-2,3-dihydro-1H,1'H-2,2'-biinden-2-yl)methyl)benzoic acid Compound 5 4-(((1S,2R)-1-hydroxy-2,3-dihydro-1H,1'H-2,2'-biinden-2-yl)methyl)benzoic acid Compound 6 6-(Methylamino)hexane-1,2,3,4,5-pentanol 4-(((1S,2S)-1-hydroxy-2,3-dihydro-1H,1'H-2,2'-biinden-2-yl)methyl)benzoate Compound 7 6-(Methylamino)hexane-1,2,3,4,5-pentanol 4-(((1S,2R)-1-hydroxy-2,3-dihydro-1H,1'H-2,2'-biinden-2-yl)methyl)benzoate Compound 8 (S)-1-Phenylethylammonium 4-(((1S,2S)-1-hydroxy-2,3-dihydro-1H,-1'H-2,2'-biinden-2-yl)methyl)benzoate Compound 9 (R)-1-Phenylethylammonium 4-(((1R,2S)-1-hydroxy-2,3-dihydro-1H,1'H-2,2'-biinden-2-yl)methyl)benzoate

The invention claimed is:
1. A compound of formula

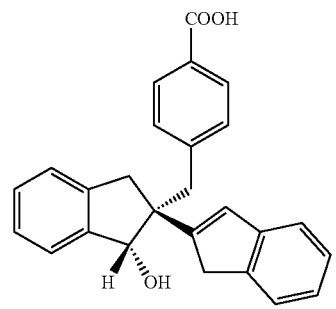 [SMILES: O=C(O)c1ccc(C[C@@]2(C3=Cc4ccccc4C3)Cc3ccccc3[C@H]2O)cc1]

and pharmaceutically acceptable salts thereof.

2. A N-Methyl-(D)-Glucamine salt compound of formula

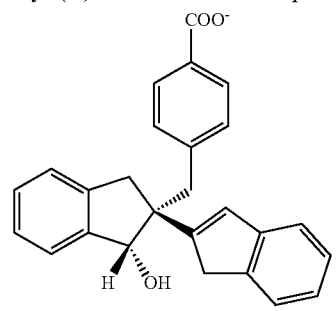

-continued

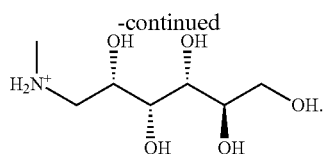
5

3. The pharmaceutical composition comprising an effective amount of a compound as claimed in claim 1 and a pharmaceutically acceptable carrier.

4. The pharmaceutical composition comprising an effective amount of a compound as claimed in claim 2 and a pharmaceutically acceptable carrier.

5. A method for the treatment of inflammatory bowel disease, comprising administering to a subject an effective amount of a compound as claimed in claim 1.

6. A method for the treatment of inflammatory bowel disease, comprising administering to a subject an effective amount of a compound as claimed in claim 2.

7. A method for the treatment of ulcerative colitis, comprising administering to a subject an effective amount of a compound as claimed in claim 1.

8. A method for the treatment of ulcerative colitis, comprising administering to a subject an effective amount of a compound as claimed in claim 2.

9. A method for the treatment of Crohn's disease, comprising administering to a subject an effective amount of a compound as claimed in claim 1.

10. A method for the treatment of Crohn's disease, comprising administering to a subject an effective amount of a compound as claimed in claim 2.

* * * * *